United States Patent [19]
Trumble et al.

[11] Patent Number: 5,888,186
[45] Date of Patent: Mar. 30, 1999

[54] MUSCLE ENERGY CONVERTER ACTIVATED ASSIST SYSTEM AND METHOD

[75] Inventors: Dennis R. Trumble; James A. Magovern, both of Pittsburgh, Pa.

[73] Assignee: Allegheny-Singer Research Institute, Pittsburgh, Pa.

[21] Appl. No.: 809,106

[22] PCT Filed: Jul. 25, 1996

[86] PCT No.: PCT/US96/12230

§ 371 Date: Mar. 5, 1997

§ 102(e) Date: Mar. 5, 1997

[87] PCT Pub. No.: WO97/04823

PCT Pub. Date: Feb. 13, 1997

Related U.S. Application Data

[63] Continuation-in-part of Ser. No. 507,853, Jul. 27, 1995, Pat. No. 5,718,248.

[51] Int. Cl.[6] .................................................... A61N 1/362
[52] U.S. Cl. .............................................................. 600/16
[58] Field of Search ........................ 600/16, 17; 601/106, 601/153; 607/1, 2, 35

[56] References Cited

U.S. PATENT DOCUMENTS

| | | | |
|---|---|---|---|
| 4,453,537 | 6/1984 | Spitzer | 600/17 |
| 5,098,369 | 3/1992 | Hgilman et al. | 600/16 |

*Primary Examiner*—William E. Kamm
*Attorney, Agent, or Firm*—Ansel M. Schwartz

[57] ABSTRACT

A system for assisting the operation of a patient's heart. The system includes a muscle energy converter which is capable of connecting to a muscle of the patient for converting energy of the muscle into a mechanical force. The system also includes a ventricular assist device connected to the muscle energy converter for receiving the mechanical force from the muscle energy converter and compressing the heart of the patient. The assist device is capable of connection and operational engagement with the heart. A method for assisting the operation of a patient's heart. The method includes the steps of converting energy from a muscle to a mechanical force with a muscle energy converter. Then, there is the step of compressing the heart of the patient with an assist device with the mechanical force from the muscle energy converter.

6 Claims, 22 Drawing Sheets

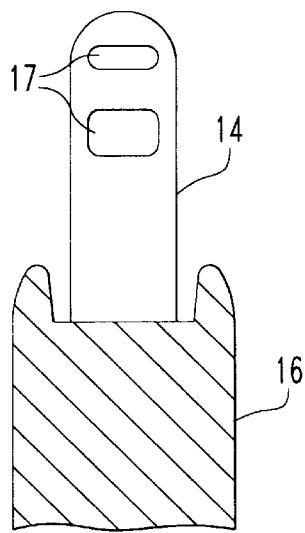
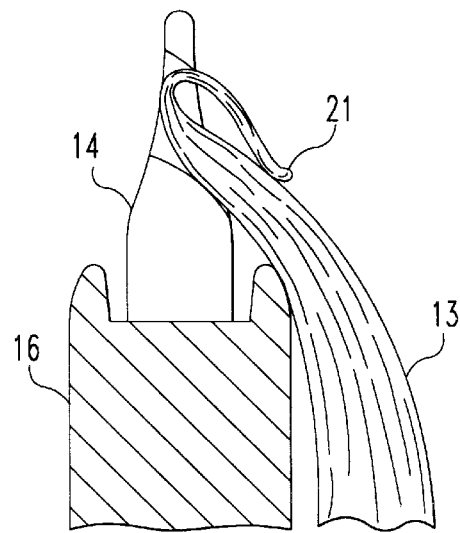
*FIG.2a*  *FIG.2b*
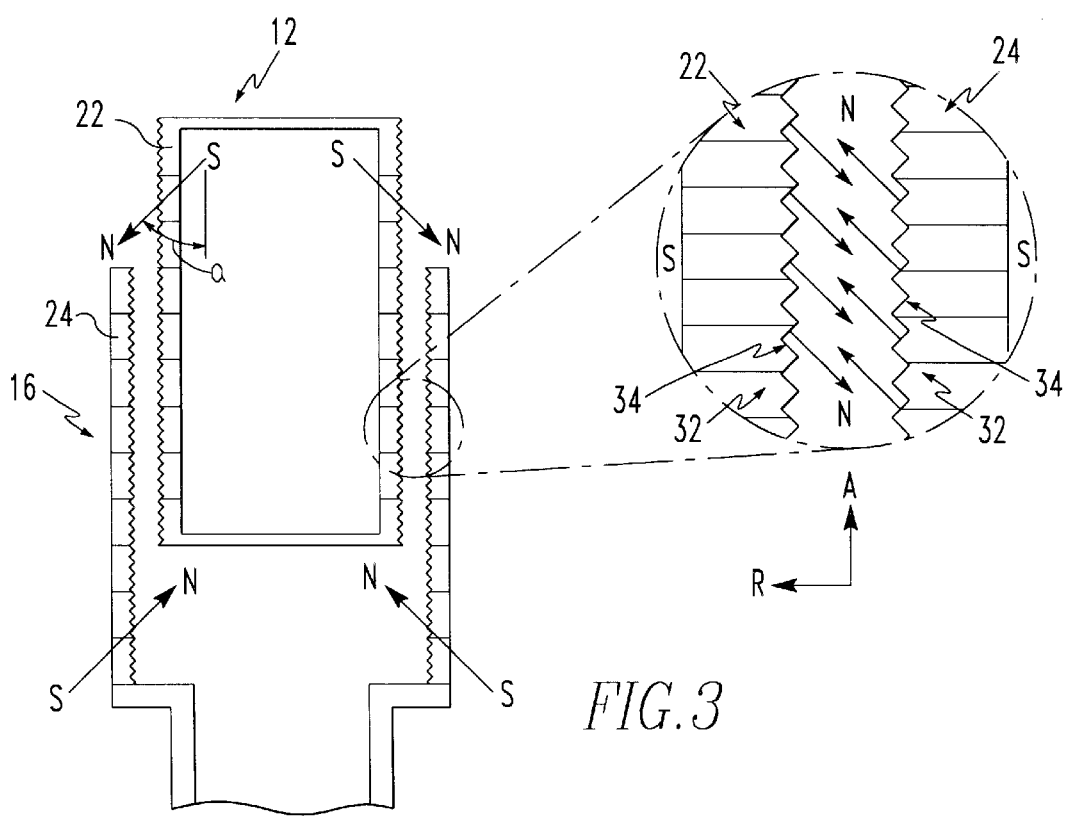
*FIG.3*

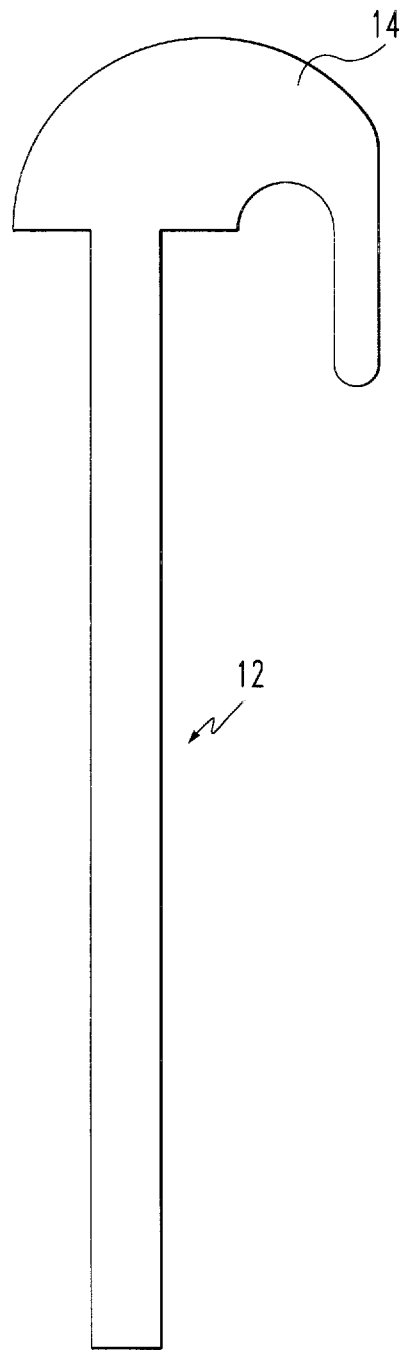 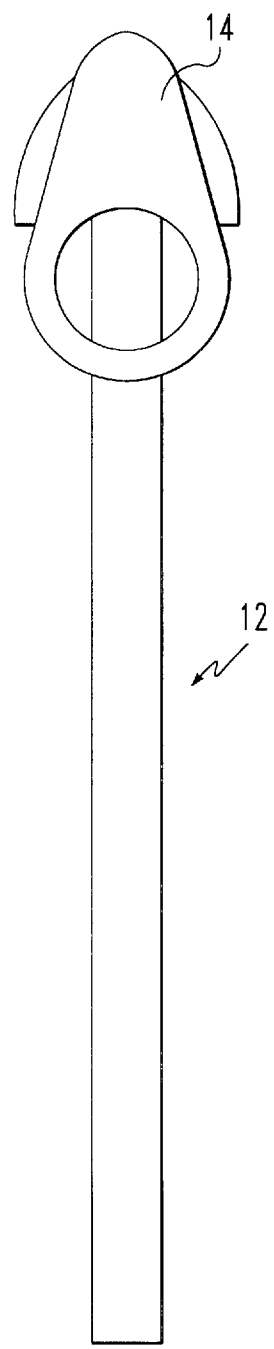
FIG.10i        FIG.10i-i

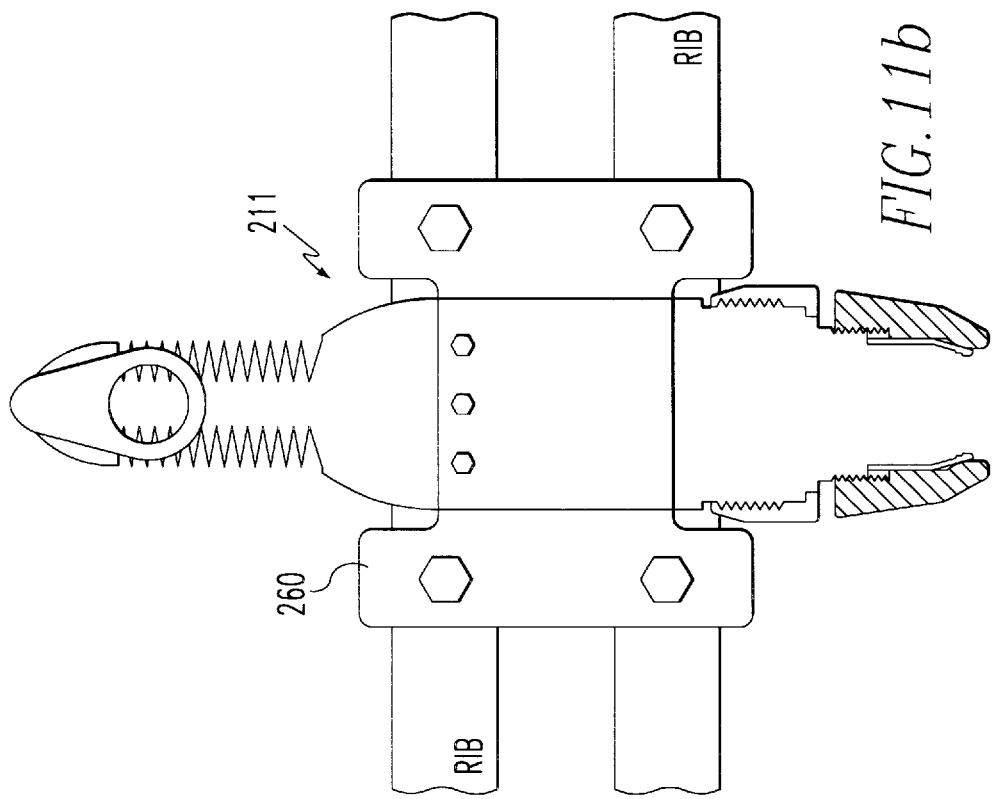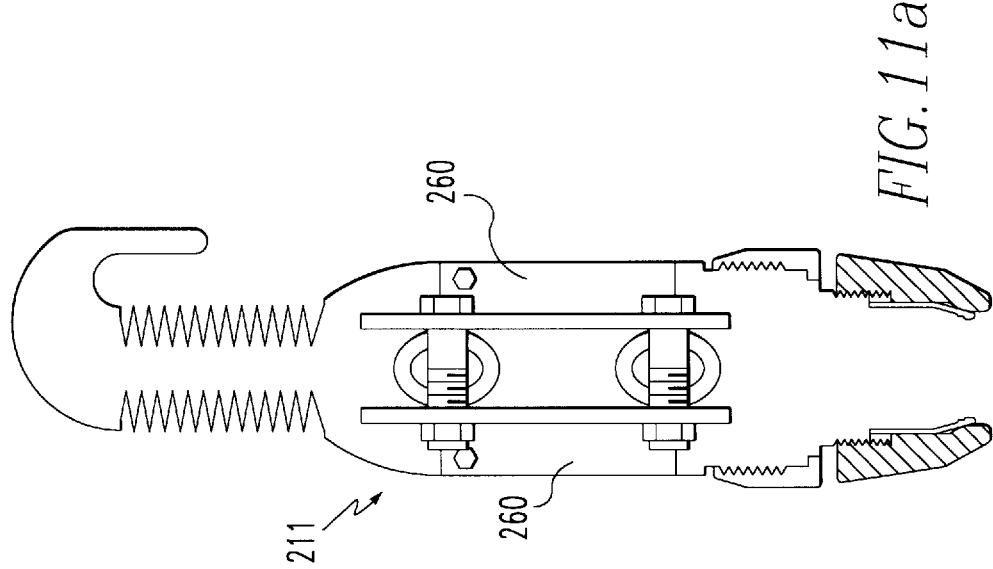

MUSCLE ENERGY CONVERTER ACTIVATED ASSIST SYSTEM AND METHOD

CROSS-REFERENCE

This application is a continuation-in-part of U.S. patent application Ser. No. 08/507,853 filed Jul. 27, 1995 now U.S. Pat. No. 5,718,248 issued Feb. 17, 1998, and claims priority from PCT/US96/12230.

FIELD OF THE INVENTION

The present invention is related to medical devices. More specifically, the present invention is related to a device for converting muscle power into alternative forms of body work.

BACKGROUND OF THE INVENTION

The idea of using endogenous skeletal muscle as an energy source for cardiac assistance is not new. Many investigators have demonstrated that untrained skeletal muscle can provide circulatory support for short periods of time (minutes to hours). However, early studies were plagued by rapid muscle fatigue which discouraged the use of skeletal muscle as a long-term energy source for biomechanical assistance. This ultimately prompted researchers to explore the possibility of conditioning skeletal muscle via chronic electrical stimulation.

The ultimate objective of chronic myostimulation is to transform muscle to a fatigue-resistant state so that it performs much like the myocardium, which is an oxidative muscle capable of continuously pumping blood. Both cardiac and skeletal muscle contain contractile proteins which transform chemical energy into mechanical work, but skeletal muscle comprises several types of muscle cells with different physiologic and metabolic characteristics. These contractile fibers may be either glycolytic (fatigue-susceptible) or oxidative (fatigue-resistant). Slow-twitch muscle is generally oxidative, while more powerful fast-twitch muscle can be either glycolytic or oxidative. In order to utilize skeletal muscle for long-term circulatory assist, a conditioning scheme is needed to convert these fibers from glycolytic to oxidative metabolism.

The feasibility of converting fast-twitch muscle fibers to fatigue-resistant slow-twitch fibers was demonstrated by Salmons and Sreter in the mid-70s. (Salmons, S., and Sreter, F. Significance of impulse activity in the transformation of skeletal muscle type. Nature, vol. 263, 30–34, 1976). Since then, interest in skeletal muscle conditioning has increased and has become a major subject of current studies. (Sreter, F., Pinter, K., Jolesz, F., and Mabuchi, K., Fast to slow transformation of fast muscles in response to long-term phasic stimulation. Experimental Neurology, vol. 75, 95–102, 1982; Macoviak, J., Stephenson, L., Armenti, F., Kelly, A., Alavi, A., Mackler, T., Cox, J., Palatianos, G., and Edmunds, L., Electrical conditioning of in situ skeletal muscle for replacement of myocardium. J. Surgical Research, vol. 32, 429–439, 1982). Recently, both Frey and Dewar have shown that a short train or "burst" of pulses is effective in producing a sustained contraction with complete conversion of skeletal muscle to fatigue-resistant fibers. (Frey, M., Thoma, H., Gruber, H., Stohr, H., Huber, L., Havel, M., and Steiner, E. The chronically stimulated muscle as an energy source for artificial organs. Eur. Surgical Research, vol. 16, 232–237, 1984; Dewar, M., and Chiu, R. Cardiomyoplasty and the pulse-train stimulator. Biomechanical Cardiac Assist, Futura Publ. Co., 43–58, 1986).

This knowledge has led to a myriad of new techniques designed to utilize the transposition of conditioned contractile tissue. Applications include cardiomyoplasty, diastolic counterpulsation, and using the muscle as an energy source to drive cardiac assist devices. To date, most attempts to harvest this new power source have involved wrapping a muscle flap around the heart, aorta or prosthetic conduit, or shaping the muscle into a neo-ventricle. (Magovern, G., Park, S., Kao, R., Christlieb, I., and Magovern, Jr., G. Dynamic cardiomyoplasty in patients. J. Heart Transplantation, vol. 9, 258–263, 1990; Pattison, C., Cumming, D., Williamson, A., Clayton-Jones, D., Dunn, M., Goldspink, G., and Yacoub, M. Aortic counterpulsation for up to 28 days with autologous latissimus dorsi in sheep. J. Thoracic Cardiovascular Surgery, vol. 102, 766–773, 1991; Mannion, J., Hammond, R., and Stephenson, L. Hydraulic pouches of canine latissimus dorsi; potential for left ventricular assistance. J. Thoracic Cardiovascular Surgery, vol. 91, 534–544, 1986; Hammond, R., Bridges, C., DiMeo, F., and Stephenson, L. Performance of skeletal muscle ventricles: effects of ventricular chamber size. J. Heart Transplantation, vol. 9, 252–257, 1990).

These efforts have met with only limited success because of insufficient power generation, slow relaxation, muscle atrophy, and thromboembolism. Wrapping the muscle flap is an inefficient means for collecting muscle energy and requires complete mobilization of the muscle, which interrupts some of its blood supply and increases the development of fibrosis. It is apparent that muscle-wrapping techniques are not the best way to harvest useful work from skeletal muscle, and that alternative pumping schemes should be explored.

Previous studies have demonstrated that certain large skeletal muscles can produce high amounts of aerobic (steady-state) energy if the muscle is left in situ and allowed to contract linearly. For example, Ugolini recently published an article describing an energetic balance of the human psoas major that predicts a steady-state power capacity of 5.19 watts. (Ugolini, F. Skeletal muscle for artificial heart drive: theory and in vivo experiments. Biomechanical Cardiac Assist, Futura Publ. Co., 193–210, 1986). This power level would be more than sufficient to drive a hydraulic artificial heart (which has a typical power requirement of <1.2 watts) if a means could be devised to efficiently convert this energy into pumping power.

Logically, one of the most effective ways to harness muscular work for this purpose would be to employ a linear arrangement with the muscle tendon detached from its original insertion point and reconnected to a hydraulic energy converter. This hypothesis has recently been tested by Sakakibara (Sakakibara, N., Tedoriya, T., Takemura, H., Kawasuji, M., Misaki, T., and Watanabe, Y. Linear muscle contraction for actuation of a muscle-powered cardiac assist device (MCAD): an ex vivo pilot study. ASAIO Abstracts, vol. 21, p. 53, 1992), who evaluated the performance of latissimus dorsi (LD) muscle in three orientations: roll (wrap) type; compressive type; and linear type. This study showed that linear actuation produced a six-fold improvement in work output versus wrap-type, and a 50% increase over the compressive arrangement.

Another study, performed by Geddes at Purdue University (Geddes, L., Badylak, S., Tacker, W., and Janas, W. Output power and metabolic input power of skeletal muscle contracting linearly to compress a pouch in a mock circulatory system. J. Thoracic and Cardiovascular Surgery, vol. 104, 1435–1442, 1992), utilized three different groups of muscles (contracting linearly) to compress a valved pouch in a hydraulic model of the circulation. Output power and metabolic input power were measured at contraction rates from 10 to 40 per minute. Muscle blood flow increased dramatically during periods of work, and fatigue was not a factor even though unconditioned muscles were used. Continuous power generation of over 2 watts was recorded for all groups, with an energy conversion efficiency approximating that of cardiac muscle (10%). Based on these data, Geddes concluded that an energy-conversation scheme should be sought in which linear shortening of skeletal muscle could be used to assist the circulation.

The concept of powering a pump with linearly contracting muscle appeared in the literature as early as 1964, when Kusserow and Clapp employed a quadriceps femoris muscle to drive a spring-loaded diaphragm pump. (Kusserow, B., and Clapp, J. A small ventricle-type pump for prolonged perfusions: construction and initial studies, including attempts to power a pump biologically with skeletal muscle. Trans. ASAIO, vol. 10, 74–78, 1964.) Since that time, a number of investigators have addressed this topic, yet no serious attempts to develop such a device were published until Sasaki in 1992. (Sasaki, E., Hirose, H., Murakawa, S., Mori, Y., Yamada, T., Itoh, H., Ishikawa, M., Senga, S., Sakai, S., Katagiri, Y., Hashimoto, M., Fuwa, S., and Azuma, K. A skeletal muscle actuator for an artificial heart. ASAIO Journal, vol. 38, 507–511, 1992.) His system employs a flexible rod, sheath, crank, and cam to transmit muscle power to a pusher-plate pump. This scheme was tested in dogs using an untrained latissimus dorsi muscle and a mock circulatory system. At 60 beats per minute, this device maintained 0.8–2.0 L/min for 200 minutes against an afterload of 75 mmHg. Output power was 2.5 mW/gram, and system efficiency approached 50%.

Most recently, Farrar and Hill developed a new muscle-powered, linear-pull energy converter for powering various implantable devices. (Farrar, D., and Hill, J. A new skeletal linear-pull energy convertor as a power source for prosthetic circulatory support devices. J. Heart and Lung Transplantation, vol. 11, 341–350, 1992.) This device consists of a metal cylinder which houses a piston-type actuator to which the muscle is attached. As the muscle contracts, up to 2 ml of hydraulic fluid is displaced into a transmission line leading to the blood pump. During relaxation, a spring is employed to assist pump filling and muscle lengthening. This device has problems, though. For instance, energy convertor components were purchased off the shelf, and no attempt was made to minimize energy losses. Consequently, the efficiency of this device was found to be only 22.5%.

Clearly, interest in muscle-powered assist devices is on the rise. However, efforts to date have produced systems that employ conventional mechanisms subject to frictional losses and component wear. Not only does this limit the lifetime of the prosthesis, but reduces the amount of work obtained from the muscle. Given the limited aerobic capacity of skeletal muscle, future research must focus on optimizing system efficiency in order to ensure long-term operation and effective muscle use.

Despite recent advances in both pharmacologic and surgical therapies for heart failure, about 250,000 Americans die each year from this condition. A totally-implantable ventricular assist device would be an effective treatment, but the complexities of transcutaneous power delivery and problems associated with blood contacting surfaces have severely limited this approach. The hydraulic ventricular assist device was developed as a means to utilize muscle power to aid the failing heart while avoiding direct contact with the bloodstream.

This method of cardiac assistance offers an attractive alternative to current long-term support schemes by eliminating the need for artificial power sources. Through this mechanism, external battery packs, power conditioning hardware, transmission coils, and internal power cells could all be replaced by natural biomechanical processes, serving to greatly enhance patient quality of life by improving reliability, eliminating external components, and reducing costs. Moreover, external cardiac compression avoids critical problems associated with man-made blood contacting surfaces (e.g., clotting and hemolysis).

SUMMARY OF THE INVENTION

The present invention is comprised of a muscle energy converter. The muscle energy converter is comprised of a piston having an attachment head for connection to a muscle. The muscle energy converter also comprises a cylinder having a chamber in which the piston is disposed. The cylinder has a port for transport of fluid in the chamber as the muscle moves the piston. Preferably, movement of the piston within the cylinder is frictionless.

The piston comprises a first magnetic section and the cylinder comprises a second magnetic section. The first magnetic section and the second magnetic section provide opposing fields to maintain the piston in proper alignment within the cylinder. Preferably, there is a rolling diaphragm sealing mechanism connected between the piston and the cylinder. The rolling diaphragm mechanism can include a first rolling diaphragm and a second rolling diaphragm spaced from and opposing the first rolling diaphragm. Preferably, the opposing fields of the first magnetic section and the second magnetic section are disposed at an angle between the axial and radial direction of the piston so that the piston is subject to both a radial aligning force and an axial preload force. For instance, the first magnetic section and the second magnetic section can have a series of ridged edges forming flat angled surfaces from which the opposing magnetic fields are emitted at an angle between the axial and radial directions. There can be nonmagnetic cover material disposed over the ridged edges to form a smooth outer surface.

The muscle energy converter preferably comprises a piston stroke regulation mechanism. The stroke regulation mechanism preferably comprises a central ring magnet fixedly connected to the piston which oppose first and second spaced portions of the second magnetic section. The ring magnet is disposed in a space between the first and second portions for providing travel. The cylinder can also comprise mounting hardware for attaching to bones in a body.

The present invention is also a method of using muscle energy. The method comprises the steps of attaching a muscle to an attachment head of a piston so that the muscle can move the piston within a cylinder to pressurize fluid within the cylinder. Then there is the step of maintaining frictionless alignment of the piston within the cylinder with opposing magnetic fields produced by first and second magnetic sections in the piston and cylinder, respectively. Preferably, there is the step of producing with the first and second magnetic sections a preload force on the piston. Preferably, after the attaching step, there is the step of using the fluid to perform work within the human body such as to pump blood.

The present invention pertains to a muscle energy converter for pumping fluid in a patient. The muscle energy converter comprises a piston having an attachment head which connects to tissue, preferably muscle. The piston also has an elongate portion having a first end and a second end. The first end is connected to the attachment head. The piston has a base connected to the second end. The muscle energy converter also comprises a housing, such as a cylinder, having a chamber. The cylinder has a piston port in communication with the chamber and an output port in communication with the chamber. The base is disposed in the chamber of the cylinder with the elongate portion extending from the base through the piston port. The base and the cylinder define a fluid cavity in the chamber in which fluid to be pumped by the piston is disposed. The muscle energy converter is also comprised of an expandable seal to position about the piston for defining a pumping cavity in which the piston moves. The expandable seal prevents fluid from entering the pumping cavity.

The present invention pertains to a method for pumping fluid in a patient. The method comprises the steps of attaching an attachment head of a piston to tissue, such as a muscle, of the patient. Next, there is the step of placing a housing, such as a cylinder, to the patient's body. The piston is disposed in and extending from the housing. Then, there is the step of introducing fluid into a fluid cavity of the cylinder. Next, there is the step of moving the piston with the muscle of the patient connected to the piston attachment head so the fluid in the fluid cavity is pumped out of the fluid cavity by a base of the piston pushing fluid out of the fluid cavity.

The present invention pertains to a muscle energy converter. The muscle energy converter comprises a piston having an attachment head for connection to tissue of a patient. The muscle energy converter also comprises a cylinder having a chamber, in which the piston is disposed. The cylinder has an outlet port for transport of fluid in the chamber as the tissue moves the piston. Additionally, the muscle energy converter comprises a mechanism for securing the cylinder to the patient.

The present invention pertains to a method of using muscle energy. The method comprises the steps of attaching a muscle of a patient to an attachment head of a piston. Next, there is the step of securing the cylinder to the body of the patient. Then, there is the step of moving with the muscle the piston within the surrounding cylinder to pressurize fluid within the cylinder.

The present invention pertains to a system for assisting the operation of a patient's heart. The system comprises a muscle energy converter which is capable of connecting to a muscle of the patient for converting energy of the muscle into a mechanical force. The system also comprises a ventricular assist device connected to the muscle energy converter for receiving the mechanical force from the muscle energy converter and compressing the heart of the patient. The assist device is capable of connection and operational engagement with the heart.

The present invention pertains to a method for assisting the operation of a patient's heart. The method comprises the steps of converting energy from a muscle to a mechanical force with a muscle energy converter. Then, there is the step of compressing the heart of the patient with an assist device with the mechanical force from the muscle energy converter.

BRIEF DESCRIPTION OF THE DRAWINGS

In the accompanying drawings, the preferred embodiment of the invention and preferred methods of practicing the invention are illustrated in which:

FIGS. 2a and 2b are schematic representations showing a muscle energy converter having an attachment head with slots for connection to a tendon.

FIG. 3 is a schematic representation showing angled ridged edges of the magnetic sections and associated angled opposing magnetic field lines.

FIG. 10i is a schematic representation of a front view of the piston.

FIG. 10j is a schematic representation of a side view of a piston.

FIG. 11a is a schematic representation of a side view of the muscle energy converter attached to a ribcage.

FIG. 11b is a schematic representation of a front view of the muscle energy converter attached to a ribcage.

DESCRIPTION OF THE PREFERRED EMBODIMENT

Figure 1:
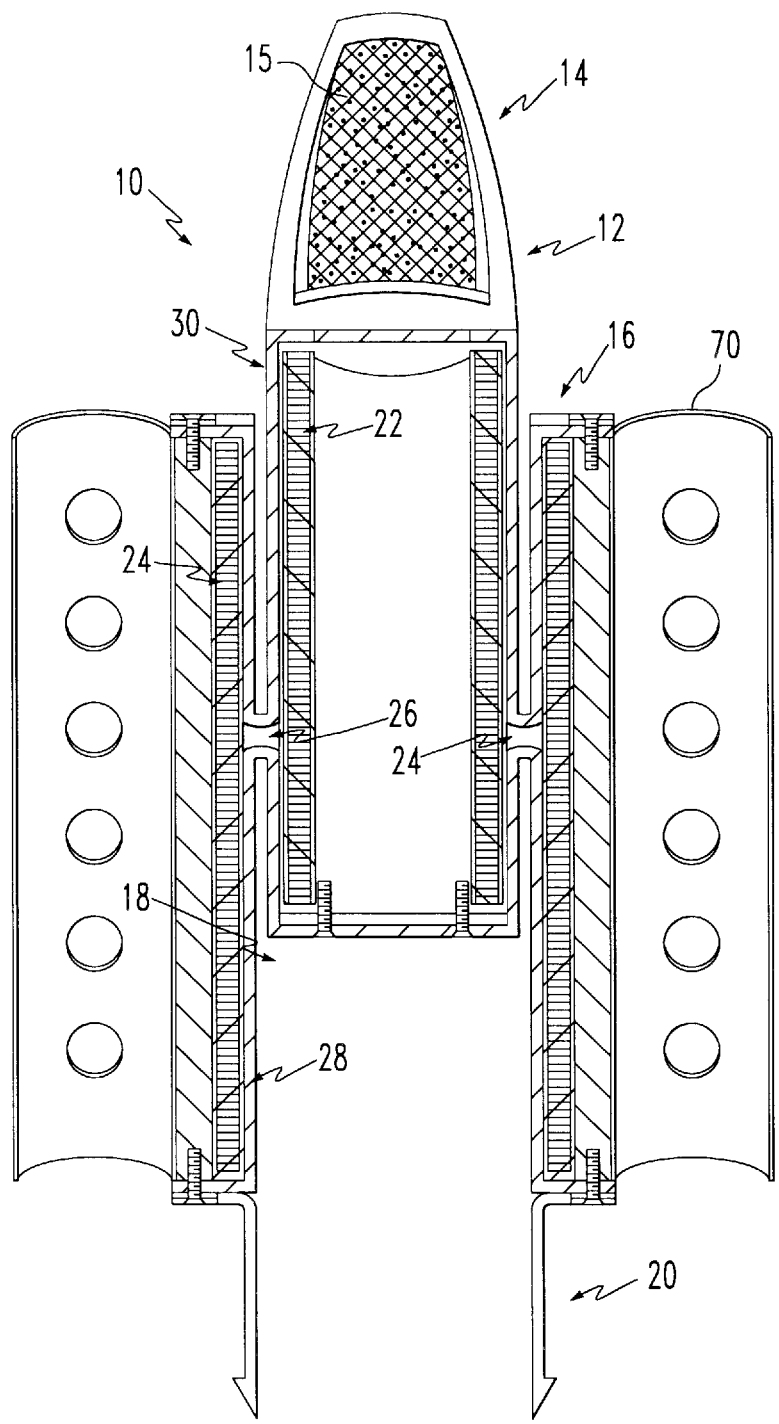
FIG. 1 is a schematic representation showing the muscle energy converter.

Referring now to the drawings wherein like reference numerals refer to similar or identical parts throughout the several views, and more specifically to FIG. 1 thereof, there is shown a muscle energy converter 10. The muscle energy converter 10 comprises a piston 12 having an attachment head 14 for connection to a muscle 13. The muscle energy converter 10 also comprises a cylinder 16 having a chamber 18 in which the piston 12 is disposed. The cylinder 16 has a port 20 for transport of fluid in the chamber 18 as the muscle moves the piston 12. Preferably, movement of the piston 12 within the cylinder 16 is frictionless. In order to maintain frictionless alignment of the piston 12 within the cylinder 16, the piston 12 comprises a first magnetic section 22 about the piston 12 and the cylinder 16 comprises a second magnetic section 24. The first magnetic section 22 and the second magnetic section 24 are disposed adjacent to each other and provide opposing fields to maintain the piston 12 in proper alignment within the cylinder 16. There can also be included a rolling diaphragm sealing mechanism 26 connected between the piston 12 and the cylinder 16. The rolling diaphragm mechanism 26 can comprise a first rolling diaphragm 28 and a second rolling diaphragm 30 spaced from and opposing the first rolling diaphragm 28.

As shown in FIG. 3, the piston 12 moves relative to the cylinder 16 in an axial direction, A, perpendicular to a radial direction R. Preferably, the opposing fields of the first magnetic section and the second magnetic section 24 are disposed at an angle, $\alpha$, between the axial and radial directions, relative to the axial direction, A, so as the piston 12 is subject to both a radial aligning force and an axial preload force by the angled opposing magnetic fields. It should be appreciated overcoming alignment problems between the piston 12 and cylinder wall 16 allows the muscle to be effectively attached as shown in FIG. 2b. Anatomically, the muscle is attached to the side of the piston surface 15. Therefore, muscle movement will impart not only a downward axial force, but a force in the radial direction as well, causing the piston 12 to tilt inside the cylinder 16 and make contact therewith. The present invention overcomes this tilting problem.

A secure attachment between the muscle tendon and piston is critical. Clearly, muscle power cannot be harnessed long-term unless this physical connection is maintained. One design includes a sewing patch as depicted in FIG. 1. The tendon can be sutured directly to this material, such as Dacron®, or Gortex®, so that the tendon covers the patch and muscle shortening moves the piston 12 into the cylinder 16.

As shown in FIG. 2a, in order to form a strong, reliable connection to the muscle 13, the attachment head 14 can have slots 17 machined through the head 14. These slots allow the tendon 21 of the muscle 13 to be pulled through and sutured back onto itself as shown in FIG. 2b. The slots 17 can be shaped and curved to automatically support the tendon 21. This design eliminates the tendon/patch interface and relies on a tendon-to-tendon anchor point which is very strong and stable.

By embedding magnetic sections 22 and 24 along the outside of the piston 12 and along the inside of the cylinder 16, respectively, the repulsive forces are utilized to maintain proper alignment despite the radial force provided by the muscle 13. Moreover, the magnetic sections 22, 24 and rolling diaphragm mechanism 26 combine to produce a muscle-powered pump with essentially no mechanical friction, making the described muscle energy converter 10 highly efficient.

A rolling diaphragm mechanism 26 requires two fundamental conditions in order to maintain nominal operation, parallel alignment of the piston 12 with respect to the cylinder 16 and a clear spacing between the cylinder 16 and piston 12. The first condition is maintained by the first and second magnetic sections 22 and 24. The second condition is preserved in vivo via the use of a second rolling diaphragm 30 inverted over the first 28, as illustrated in FIG. 1.

The second (external) rolling diaphragm 30 serves to keep the first rolling diaphragm 28 free from biological debris, so that it will continue to roll smoothly. Without this protection, blood products would likely build up between the first rolling diaphragm 28 and the walls of the piston and cylinder, causing the rolling diaphragm 28 to contact itself and eventually foul.

The second external rolling diaphragm 30 can be made an integral part of an outer coating which envelopes the entire pump 10. The action of the piston 12 during the up-stroke (i.e. diastole) serves to expel any foreign matter trapped within the convolution of the external rolling diaphragm 30, thereby keeping the first rolling diaphragm 28 clean.

It is desirable to have a preload force against the piston 12 to provide balance with the muscle (i.e. to pull the muscle back to length). To eliminate any springs in the device, the configuration of the magnetic sections 22 and 24 is preferably designed so that the opposing fields approach one another at an angle, $\alpha$, rather than perpendicular to the side walls, as shown in FIG. 3. The axial direction is shown by arrow A, while the radial direction is shown by arrow R.

Figure 4A:
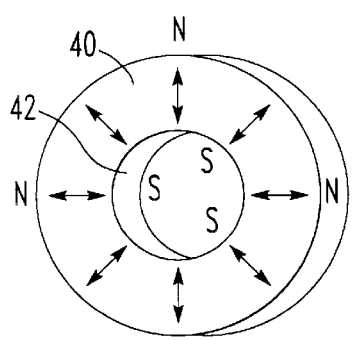
FIGS. 4a–4e are schematic representations showing fabrication of ring magnets to form cylindrical magnetic sections with angled ridges.
Figure 4B:
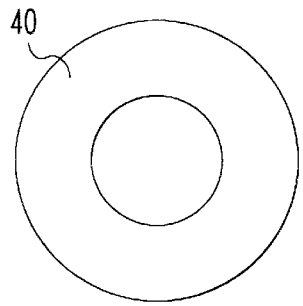
Figure 4C:
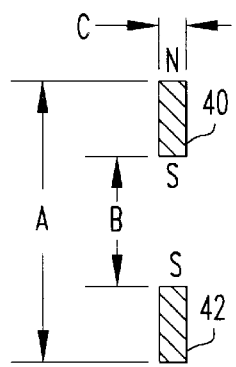
Figure 4D:
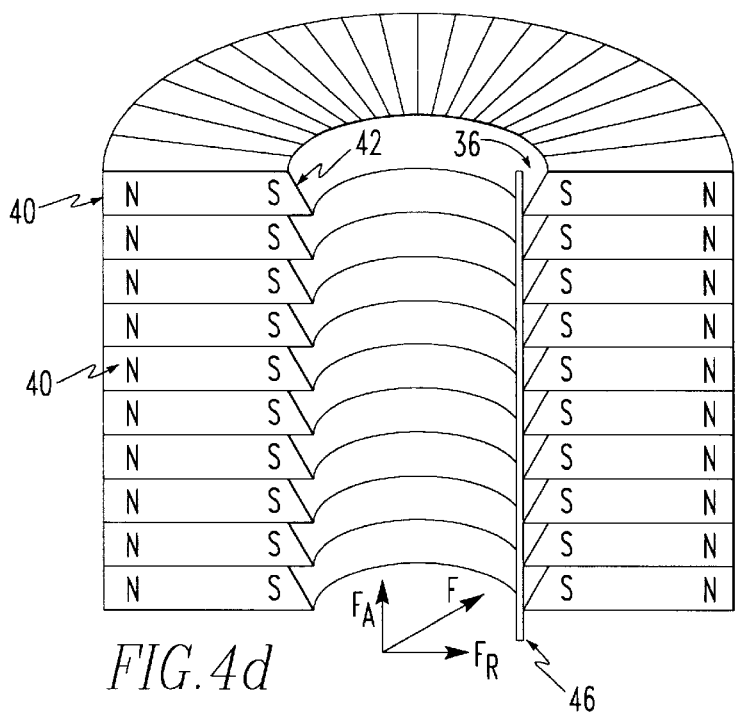
Figure 4E:
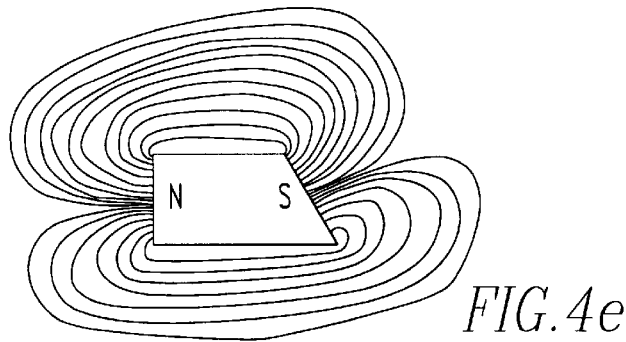

To accomplish this magnetic angle, $\alpha$, the inner surface of the first magnetic section 22 and the second magnetic section 24 have ridged edges 32 to provide a flat surface 34 perpendicular to the desired angle of magnetization, $\alpha$, as shown in FIG. 3. This is necessary due to the fact that magnetic flux lines always leave and enter the surfaces of ferromagnetic materials at right angles, as shown in FIG. 4e.

This angled magnetic configuration creates repulsive forces oriented both radially and axially. The radial component serves to maintain piston 12 alignment within the cylinder 16. The axial component provides the force required to return the piston 12 to the loaded position between contractions.

The magnitude of these forces is a function of magnetic field strength, field orientation and magnet separation. Preferably, the radial force vector, $F_R$ in FIG. 4d, is made as large as possible since it does not hinder axial motion. The axial force vector, $F_A$, must be small enough to allow muscle shortening against the afterload, yet be large enough to quickly return the muscle its original length.

The ridged edges 32 of each magnetic section 22 and 24 are preferably filled with a non-magnetic material 36 to form a smooth outer surface. This is to prevent chipping should the piston 12 and cylinder 16 come in contact and also provides a better surface for the rolling diaphragms, 28 and 30, to conform to.

In order to form the ridged edges 32 efficiently, they can be formed using the following steps using stacked ring magnets 40, as shown in FIG. 4:

1. Start with a radially-magnetized ring washer 40 of NdFeB or SmCo, as shown in FIGS. 4a–4c where, for example, A is 2.5 cm, B is 1.5 cm and C is 0.1 cm.
2. Machine the inner surface 42 of the ring 40 to some angle α (e.g. 15°).
3. Stack a number of these rings 40 to form a cylinder as shown in FIG. 4d, where $F_R$ is the radial force vector, $F_A$ is the axial force vector and F is the total force vector. The magnetic field is directed so that the majority of force is directed radially and a smaller component is directed axially (for α=15°, $F_R$=Fcos 15°=0.96F and $F_A$=Fsin 15°=0.25F).
4. Fill ridged edges 32 with non-magnetic material 36 to protect from chipping (without reducing the inner diameter).
5. Coat the entire surface with a thin layer of non-magnetic material 46 (e.g. aluminum) to strengthen and stabilize the structure.
6. Repeat steps 1–5 with smaller rings 40 to make the first magnetic section 22 for the piston 12, (with the exception that the outermost surface is machined to some angle—not necessarily equal to α).

By starting with radially-magnetized rings 40, which is a common configuration used by manufacturers, cylindrical magnetic sections 22 and 24 can be easily assembled by simple machining and stacking techniques. The resulting magnetic field can be manipulated by taking advantage of the fact that magnetic lines of force exit and enter ferromagnetic materials at right angles. The direction of the magnetic fields depends upon the angle at which the rings are machined, as shown in FIG. 4e.

The dynamic characteristics of the piston/cylinder system can be altered by changing the angle, α, of machining the rings 40, the outer diameter A, inner diameter B and thickness, C, of the rings 40, the magnetic materials employed, or the axial distribution of the rings 40.

Figure 5:
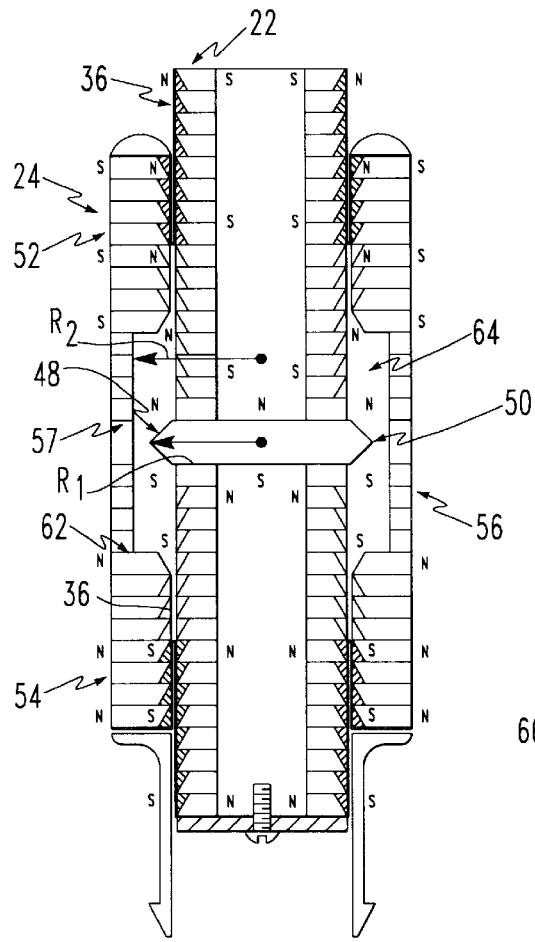
FIG. 5 is a schematic representation showing an embodiment of the muscle energy converter having a stroke regulation mechanism.

Should the piston 12 be allowed to move freely along its long axis, the rolling diaphragms 28, 30, could completely unroll and possibly bind the system. To eliminate this problem, an internal stroke regulator mechanism 48 is disclosed. The mechanism 48, as shown in FIG. 5, preferably comprises a central disc magnet 50 having a radius, $R_1$, slightly larger than an internal radius, $R_2$, of two separated portions 52, 54 of the second magnetic section 24 of the cylinder 16. The central disc 50 is positioned in the center of the piston 12. The second magnetic section 24 is divided into two portions 52, 54. There can be a two-piece spacer 56 between the two portions 52, 54. The central disc magnet 50 is magnetized so that, for example, its North pole faces the top of the device and its South pole is directed toward the I/O port 20. The magnets of the first portion 52 positioned at the top of the cylinder 16 have their North poles facing the piston/cylinder gap. This magnetic orientation is reversed for the magnets of the second portion 54 at the bottom of the cylinder 16. The length of the spacer 56 determines the distance the piston 12 is allowed to travel.

Figure 6:
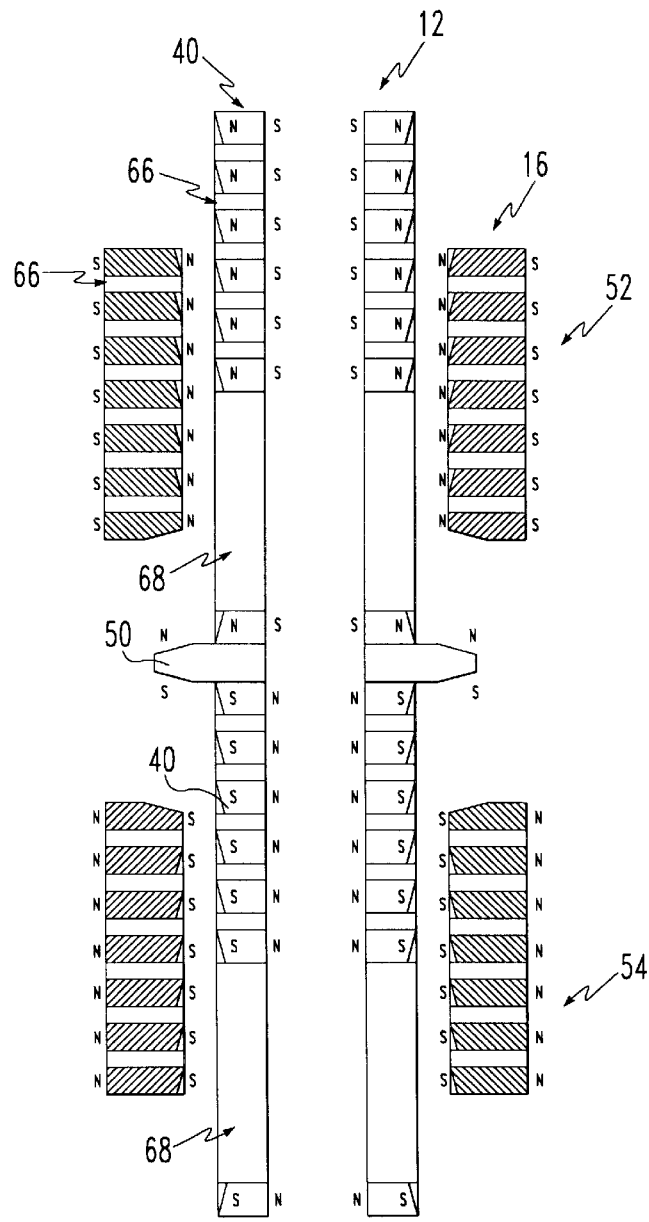
FIG. 6 is a schematic representation showing the muscle energy converter with spacers between the ring magnets to alter the magnetic dynamics.
Figure 7A:
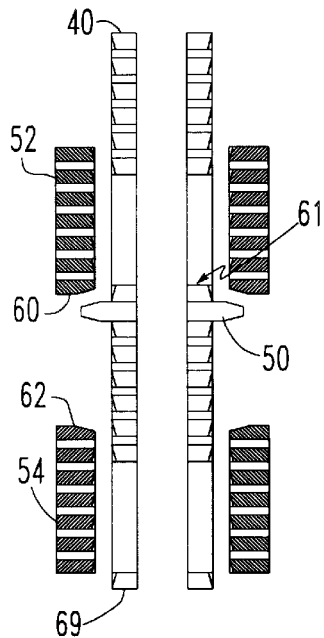
FIGS. 7a–7c are schematic representations showing the extension through compression cycles of the muscle energy converter.

As illustrated in FIG. 7a, as the piston 12 travels toward its preloaded position (extending out of the cylinder top), the North pole of the central disc magnet 50 is brought into close proximity to the North poles of the magnets of the first portion 52, slowing its motion. When the disc 50 closes to within 1 mm of the bottom-most magnet of portion 52, the repulsive forces and passive muscle tension will balance the axial preload forces and the piston 12 will stop. The bottom ring magnet 60 of first portion 52 is machined so that its North pole is directed against the central disc magnet opposite the direction of the other magnets in the first portion bearing stack 52, as shown in FIG. 6.

Figure 7B:
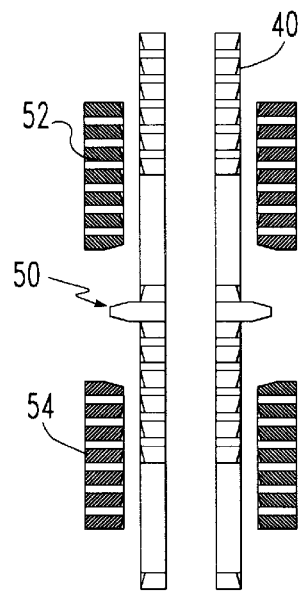
Figure 7C:
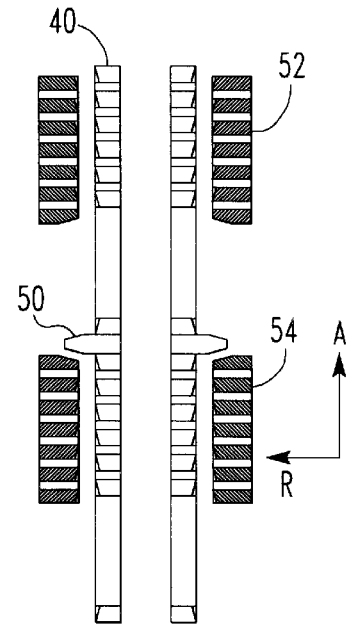

During compression (muscular contraction), as shown in FIG. 7c, the South pole of the central disc magnet 50 is brought into close proximity to the South poles of the bearing magnets of the second portion 54, again slowing its motion. When the disc 50 comes within ⁻1 mm of the upper-most bearing magnet 62 of the second portion 54, the repulsive forces will combine with the axial bearing forces to balance the compression force of the muscle and stop the piston 12. The ring magnet 62 on top of the second portion is machined so that its South pole is directed against the like pole of the central disc magnet 50 the same direction as the other magnets on the stack.

Figure 9:
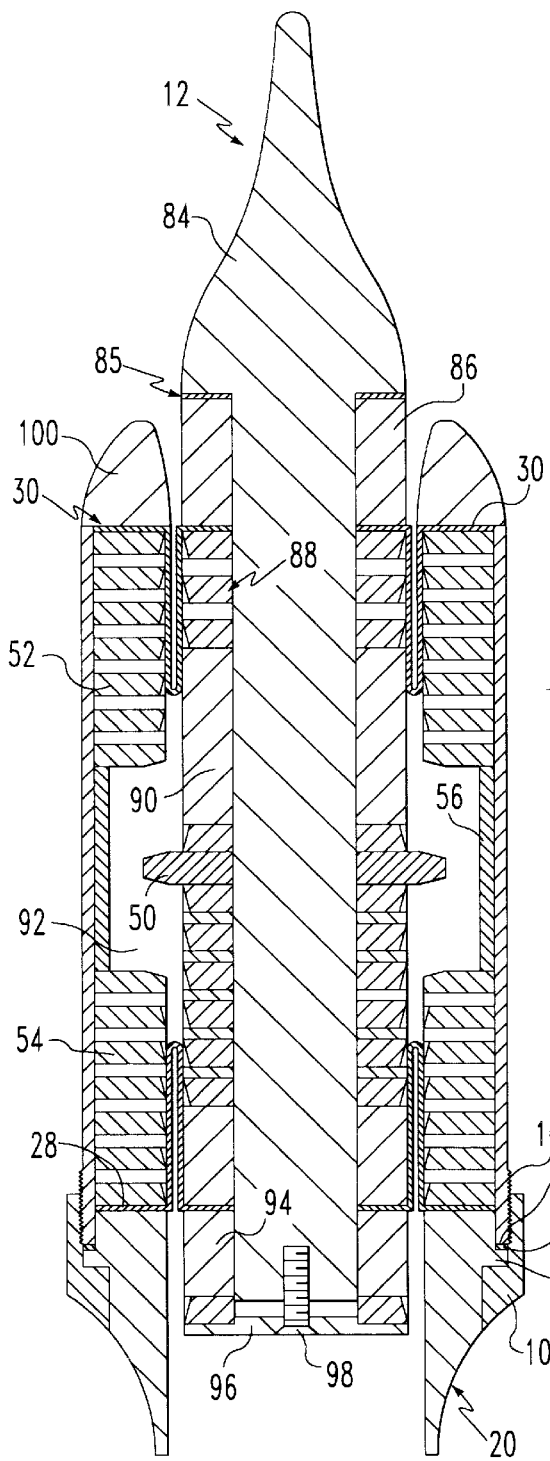
FIG. 9 is a schematic representation showing a preferred embodiment of the muscle energy converter.

This construction shown in FIGS. 5 and 9 provides axial stabilization with no contacting surfaces and a simple means to assemble and disassemble the device. This construction also maintains radial stabilization at the top and bottom where it is needed the most and separates the rolling diaphragms 28 and 30 to further enhance radial stability. This design also provides access to the inside of the device to allow examination of its parts or introduction of internal bearing fluid (if necessary). It has been discovered that stacking of ring magnets reduces the field throughout the central portion 64 of the first magnetic section 22 of the piston 12. This phenomenon is presumed to be caused by the opposing magnetic forces generated from neighboring magnets in the stack. Juxtaposition of opposing magnets can reduce the alignment of magnetic domains within individual neodymium/iron rings, thereby reducing its overall magnetization. The magnets of the central portion 64, weakened by their neighbors, are more susceptible to being overpowered by the field of the first and second portions 52, 54 of the cylinder 16. The presence of piston magnets above and below the cylinder stack, as shown in FIG. 5, produce opposing axial forces that reduce the preload of the device. In fact, it has been discovered that the total axial preload force reverses direction when the weakened central rings of the first magnetic sections 22 approach the top of the cylinder stack and the stronger end magnets approach the bottom.

As shown in FIG. 6, in order to minimize the demagnetization effects imposed on the stacked rings, spacers 66 can be introduced into the bearing design. Preferably, each spacer 66 will serve to separate the magnetic rings' a desired distance and have a relative permeability of roughly 1.0. A low permeance is preferred to direct the lines of force into the piston/cylinder gap 68 before returning to their opposite pole, thereby maximizing the repulsion between piston 12 and cylinder 16.

Selected sections of the piston 12 can be replaced with non-magnetic segments 68 to eliminate forces which counteract the preload needed to extend the piston 12. This embodiment does not seriously impair lateral bearing forces because the remaining magnets still provide significant support throughout the pump cycle.

Note that, as shown in FIG. 7a, the central magnetic disk 50 combines with its neighboring magnet above 61 and the ring magnet 69 stationed at the bottom of the piston 12 to balance the preload forces present at the top of the stroke (full extension). At full compression, FIG. 7c, the magnetic disc 50 is repulsed to add preload force and counteract the force of the muscle.

Preferably, magnets are made from Cookson's Bremag (bonded neodymium iron boron) and can be readily machined to the configuration. The specific ring magnets depicted are as follows:

Modified Cylinder magnets #NB048A manufactured by Dexter Magnetics, Inc.:
A: 1.81"
B: 0.0710"
C: 0.079"
Piston magnets #NB047C
A: 0.598:
B:0.335"
C: 0.098

Cylinder gap (equal to the separation of segments 52 and 54): 0.866" (2.2 cm)

Diaphragm: 4-71(60)70-BBJ-1 manufactured by Bellofram Corp.

(maximum stroke length=0.98" (2.49 cm))

Figure 7D:
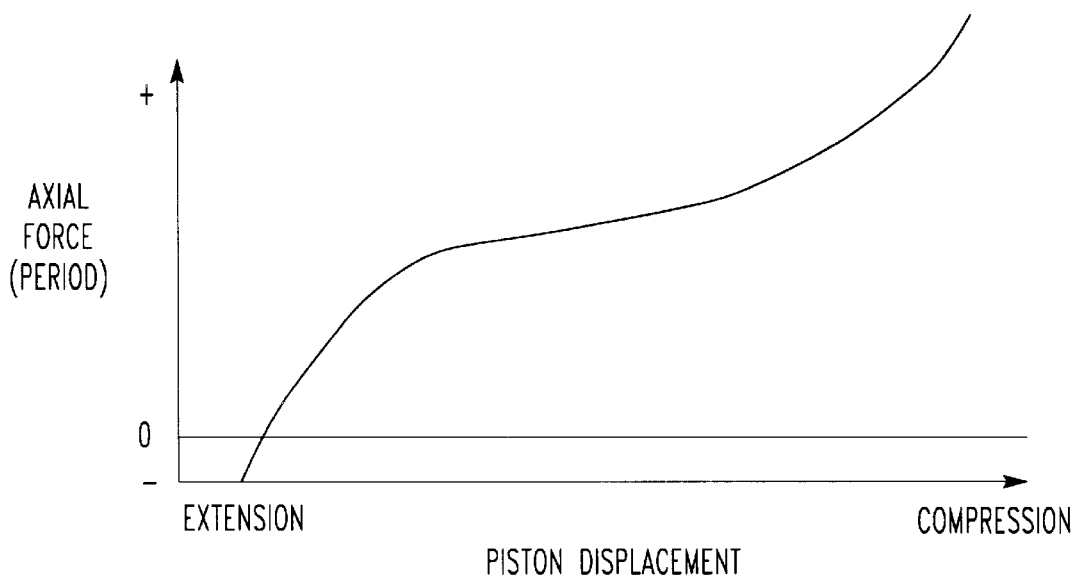
FIG. 7d is a graph showing axial preload force vs. piston displacement of the muscle energy converter.

The spacer design alters the force/displacement curve to approximate the graph shown in FIG. 7d. At full extension, (FIG. 7a), the "braking" forces of the central disc 50 and second portion ring magnets counter-balance the preload forces (resulting in zero total axial force). As the piston 12 moves into the chamber 18 (FIG. 7b), the braking force rapidly decreases and the preload force intensifies as more magnets come into close proximity (some rippling may occur due to the "lumpy" field produced by the magnet stacks).

Near full compression, as shown in FIG. 7c, maximum axial forces (due to magnet overlap) combine with disc 50 braking forces to produce a large preload force that stops the piston 12 and ultimately reverses its direction. The disc 50 braking forces act over a short distance and come into play only at the extremes of the piston stroke.

The present invention is also a method of using muscle energy. The method comprises the steps of attaching a muscle to an attachment head of a piston so that the muscle can move the piston within a cylinder to pressurize fluid within the cylinder. Then there is the step of maintaining frictionless alignment of the piston within the cylinder with opposing magnetic fields produced by first and second magnetic sections in the piston and cylinder, respectively. Preferably, there is the step of producing with the first and second magnetic sections a preload force on the piston. Preferably, after the attaching step, there is the step of using the fluid to perform work with the human body such as to pump blood.

Figure 8:
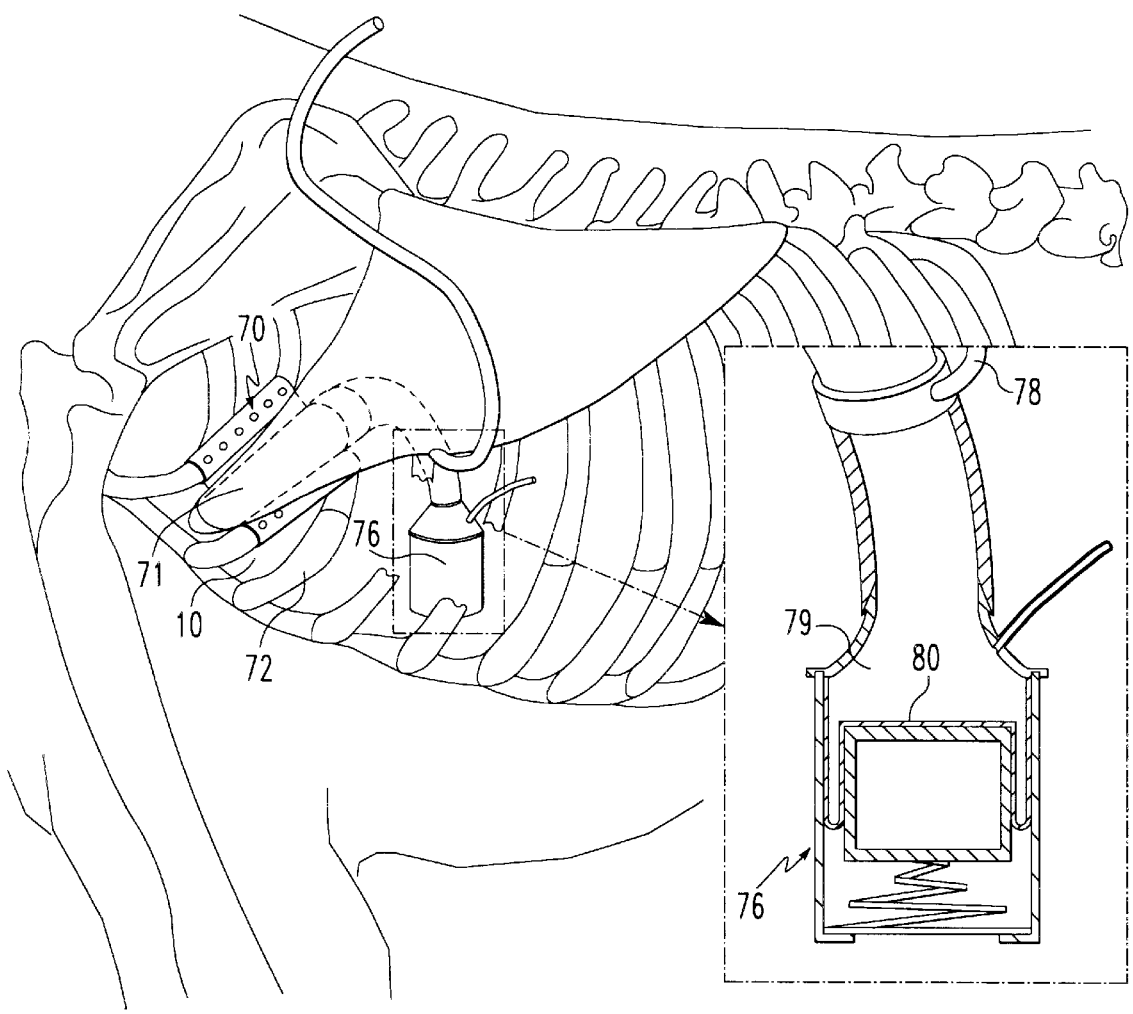
FIG. 8 is a schematic representation showing the muscle energy converter implanted in a canine for experimentation.

In order to test the invention, it can be implanted in a dog as shown in FIG. 8 which shows a proposed experimental arrangement. The cylinder 16 is attached between the ribs 72 with rib support brackets 70. The head 14 is attached to the latissimus dorsi muscle 71. Hydraulic fluid is moved and pressurized by movement of the muscle. The fluid 79 flows into an implanted afterload device 76 and is measured with flow probe 78. Rolling diaphragm 80 seals the afterload device 76. Infusion port 82 is provided for transference of hydraulic fluid 79.

In a preferred embodiment of the inventions, as shown in FIG. 9, the piston 12 is comprised of a piston shaft 84 which extends through the cylinder 16. Disposed about the shaft 84 is a polyurethane washer 85 and an upper magnetic piston stack 86, then an end (flange) of rolling diaphragm 30, followed by an upper portion 88 of the piston magnetic section 22 and then a central nonmagnetic piston stack 90. A lower portion 92 of the piston's magnetic section having the central ring magnet 50 is disposed about the piston shaft 84 followed by a lower magnetic piston stack 94. The entire piston assembly is held stacked together with a piston clamp plate 96 and a piston clamp bolt 98.

The cylinder 16 is comprised of a cylinder housing 100, a first magnetic portion 52, a one-piece spacer cylinder 56 and a second magnetic portion 54. The port 20 is connected to a threaded end 102 of the cylinder housing 100 with a threaded collet 104. An O-ring 106 is disposed between the cylinder housing 100 and the port 20. In order to fluidically seal the piston 12 to the cylinder 16 in a frictionless manner, first and second rolling diaphragms 28 and 30 are used.

The assembly of the muscle energy converter 10 as shown in FIG. 9 can be as follows:

1. slide polyurethane washer 85 against the underside of head 14 of the piston shaft/head assembly 84;
2. slide upper piston stack 86 against washer 85 and piston shaft/head assembly 84 noting proper magnet orientation;
3. place upper rolling diaphragm 30 inside the cylinder housing 100 so that its flange covers the inner ceiling of the housing 100 (rolling diaphragm not convoluted);
4. slide upper cylinder stack 52 into the cylinder housing 100 so that it compresses the upper rolling diaphragm flange 30 against the housing 100 noting proper magnet orientation;
5. slide spacer cylinder 56 into the cylinder housing 100 so that it rests against the upper cylinder stack 52;
6. slide piston shaft/head assembly 84 with washer 85 and upper piston stack through the opening of the upper rolling diaphragm 30 so that the upper piston stack 86 rests within the side walls of the upper rolling diaphragm 30;
7. slide the central piston stack 90 onto the piston shaft assembly 84 until it compresses the upper rolling diaphragm 30 against the upper piston stack 86 noting proper magnet orientation;
8. move the partially-assembled piston 12 toward the top of the cylinder housing 100 so that the upper rolling diaphragm 30 forms a convolution (i.e. folds over on itself);
9. slide the lower cylinder stack 54 into the cylinder housing 100 so that it rests against the spacer cylinder 56 noting proper magnet orientation;
10. place the convoluted lower rolling diaphragm 28 over the piston shaft assembly 84 so that its sidewalls are completely supported by the central piston stack 90 and the lower cylinder stack 54;
11. slide the lower piston stack 94 onto the piston shaft assembly 84 until it compresses the lower rolling diaphragm 28 against the central piston stack 90 noting proper magnet orientation;
12. center the piston clamp plate 96 against the bottom of the lower piston stack 94;
13. thread the piston clamp bolt 98 through the recessed central aperture of the piston clamp plate 96 and into the threaded piston shaft assembly 84;
14. tighten the piston clamp bolt 98 so that all piston components are pressed tightly together and both rolling diaphragm heads are held securely between the piston stacks 86, 90, 94;
15. place the O-ring 106 in the upper ridge 107 of the outlet port 20;
16. place the inlet/outlet port 20 against the flange of the lower rolling diaphragm 28 so that the O-ring 106 opposes the lower rim 109 of the cylinder housing 100;
17. place the threaded collet 104 over the inlet/outlet port 20 and secure to the cylinder housing 100 by screwing the collet 104 onto the threads of the cylinder housing 100; and 18. tighten the threaded collet 104 so that the internal cylinder components 52, 54 and 56 are compressed between the cylinder housing (100) and inlet/outlet port 20 and both rolling diaphragm flanges 28, 30 are held securely between the cylinder stacks and housings 100, 20.

Preferably, the components are machined from non-magnetic materials (e.g. aluminum, titanium, 300-series stainless steel, plastic, etc.) Materials of varying permeability may be chosen for specific components as a means of manipulating the magnetic field.

Figure 10:
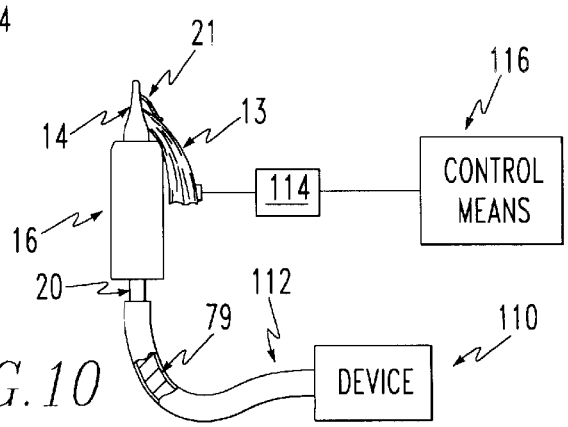
FIG. 10 is a schematic representation showing the muscle energy converter in a complete system to power a device.

A complete system using the muscle energy converter 10 is shown in FIG. 10. The muscle 13 is stimulated using a stimulator 114 controlled by control means 116. Several different implantable pulse-train generators (IPGs) can be employed to stimulate and condition skeletal muscle for powering the muscle energy converter 10. The Itrel 7420 (Medtronic) neurostimulator is an implantable pulse-train generator that has been used in a variety of muscle training protocols. However, it cannot be synchronized with the heart, and therefore is not suitable for experiments using muscle for ventricular assistance. Many studies have utilized the expanded capabilities of the Medtronic SP1005 cardiomyostimulator, which can generate a wide variety of pulse trains in synchrony with the heart or as infrequently as every fourth beat. Two other cardio-synchronous muscle pacers are also frequently utilized: the Prometheus IPG (Medtronic) and the Telectronics CSM. Both offer a wide range of stimulation variables, thereby permitting various training and pacing regimens. These variables include: synchronization ratio (as low as every tenth beat); burst duration; pulse interval; pulse width; burst delay; and pulse amplitude. In addition, the Prometheus IPG has the unique ability to automatically adjust burst duration and delay as a percentage of the sensed cardiac cycle.

Unlike cardiac muscle, skeletal muscle does not behave as an electrical syncytium. Therefore, coordinated contraction is most efficiently achieved through stimulation of the motor nerve. In testing, seven canine latissimus dorsi muscles (LDM) were used to evaluate the effects of electrode position and stimulation profile on contractile response. Two types of perineural (PN) bipolar leads were placed on the thoracodorsal nerve near its junction with the LDM. Four unipolar intramuscular (IM) electrodes were woven transversely across the LDM. The first was placed at the most proximal bifurcation of the nerve, while the other three equally divided the LDM into thirds. Peak isometric contractile force was measured during single and burst stimulations ranging from 0.1 to 10.0 volts. Each pulse train consisted of six pulses delivered at a frequency of 30 Hz.

The threshold voltage (minimum voltage required to produce measurable tension), plateau voltage (minimum voltage necessary for maximum force generation), and maximum force were measured and are summarized in Table 1. Perineural leads resulted in significantly lower threshold and plateau voltages than did any IM electrode pair in both single and burst stimulation modes. Threshold and plateau voltages progressively rose as the distance from the neurovascular pedicle to the IM electrode pairs was increased. As compared to a single stimulus, burst stimuli achieved a significantly higher maximal force, no matter which electrodes were used.

TABLE 1

Stimulation/Contraction Parameters of Perineural and Intramuscular Leads

| Lead Type | Stimulation Mode | Threshold Voltage | Plateau Voltage | Max. Force (Newtons) |
| --- | --- | --- | --- | --- |
| 360° Perineural | Burst | 0.2 ± 0.04 | 0.7 ± 0.06 | 37 ± 3 |
| 180° Perineural | Burst | 0.4 ± 0.1 | 1.0 ± 0.2 | 38 ± 4 |
| IM Proximal | Burst | 1.7 ± 0.2 | 4.7 ± 0.7 | 35 ± 5 |
| IM Middle | Burst | 3.5 ± 0.3 | 9.7 ± 0.1 | 26 ± 5 |
| IM Distal | Burst | 4.1 ± 0.6 | 9.6 ± 0.2 | 15 ± 4 |
| All | Burst | 1.9 ± 0.2 | 5.3 ± 0.5 | 32 ± 2 |
| All | Single | 2.1 ± 0.2 | 4.7 ± 0.4 | 9.8 ± 4 |

Results expressed as mean = SEM

This study (Furnary, A., Trumble, D., Vu, T., Magovern, G., and Kao, R. Perineural leads and burst stimulation optimize contraction of skeletal muscle. ASAIO Transactions, vol. 37, 164–166, 1991) clearly demonstrates that PN leads are more efficient for muscular excitation. Moreover, these leads have been used in chronic studies for up to one year without detrimental effects on the motor nerve. Burst stimulation elicits greater maximal force than a single pulse and does so independent of electrode type.

In an isometric endurance study (Kao, R., Trumble, D., Magovern, G. Fatigue resistance muscle with preserved force and mass for cardiac assist. J. Cardiac Surgery, vol. 6, 210–217, 1991), six sheep under general anesthesia had their left and right LD muscles mobilized for perineural electrode and pulse generator implantation. Each muscle was encased in surgical membrane to avoid tissue adhesions and revascularization. After a 10-day recovery period, the left side muscles were paced at a gradually increasing rate (30–120 pulse-trains/min) over a three-month period. Each burst stimulus consisted of six pulses delivered at 30 Hz over a 190-msec time interval. At four months after operation, the tendinous end of each LD muscle was freed from its humeral insertion and attached to a strain gauge transducer for isometric force measurements. Both left and right muscles from each animal were stimulated to contract for 2 hours before being isolated, trimmed, and weighted. Frozen tissue biopsies were used to determine creatine phosphate, adenosine triphosphate (ATP), lactate, and glycogen content as well as myosin ATPase and succinate dehydrogenase (SDH) activities.

The arterial diameter in the conditioned muscle was 30% larger than that of the control muscle and had a 40% higher blood flow at rest. A three- to five-fold increase in blood flow during the endurance test was observed. A steady-rate isometric force of 3.05N was achieved in the conditioned muscle versus 0.79N for the control group. The mass and cross-sectional areas of conditioned and unconditioned muscles were similar. Electric conditioning increased fatigue-resistant fiber content from 33% to 92%, as evidenced by myosin ATPase activity. During the early phases of the fatigue test, a lower lactate production was found for the conditioned muscles, indicating the increased oxidative capacity of the transformed muscle. This was also confirmed by the higher oxygen uptake and SDH activity. This study indicates that it is possible to produce fatigue-resistant muscle with preserved muscle mass and significant contractile strength.

Isometric testing measures muscular strength, but work production and contractile speed cannot be determined because the muscle is not allowed to shorten. To eliminate this problem, a muscle-actuated piston pump (MAPP) was designed and constructed. (Trumble, D., Kao, R., Magovern, G. Quantification of skeletal muscle work capacity for circulatory assistance. Cardiovascular Sci. & Tech.: Basic and Applied II, 388–389, 1991.) This device quantifies the amount of external work extracted from paced muscle by efficiently converting energy into the hydrodynamic pressures and flows of a Penn State mock circulatory system.

The muscle is attached to the MAPP by a thin cable which traverses a stationary pulley and is fixed to one end of a lever. Attached to the opposite end of the lever is a piston mounted on a rolling diaphragm. As the muscle contracts, it pulls up on one end of the lever, forcing the piston down an equal distance. Beneath the piston lies a fluid-filled chamber with a tilting-disc valve placed at each end to provide uni-directional flow. Pressures are measured within the pump chamber and in the systemic and venous compliance chambers of the mock loop. Flow is measured using an ultrasonic flowprobe positioned at the outlet port of the MAPP. Bench tests have shown no discernible energy losses within the MAPP system. This is due primarily to the frictionless nature of the rolling diaphragm which supports the piston head. As a result, the energy produced by the muscular contraction may be measured directly in the form of pressures and flows.

Six canine LD muscles were evaluated using the MAPP/mock loop system. The muscles were not mobilized, thereby preserving their collateral circulation. A customized stimulating lead was implanted over the thoracodorsal nerve. The tendinous insertion of the LD to the humerus was transected and connected to the MAPP. Preload was adjusted to return the LD to its in-situ length, and pulse trains were delivered at a rate of 60 per minute. Each burst stimulus consisted of 11 pulses delivered at a rate of 43 Hz. Under these conditions, average peak power levels reached 10.75 watts, while mean power during shortening exceeded 5.5 watts. This level of performance easily exceeds that of many previous studies, and reflects the improved muscle perfusion that results when the LD is left in situ and not mobilized from the chest wall on a single vascular pedicle. These data are especially encouraging since the average mass of these muscles was only 200 grams.

A typical left ventricle (350 g) must deliver approximately 3.3 watts during systole to move 5.0 L/min against a pressure gradient of 100 mmHg. These canine LD muscles generated 38% more energy with 43% less mass. These results imply that large skeletal muscle (>450 g) could generate enough mechanical work to support the entire circulation (even if the conditioning process weakens the muscle by as much as 50%).

As shown in FIG. 10, the muscle energy converter may be used to power a variety of devices 110 including:

a) intra-aortic balloon pumps wherein the muscle tendon 21 is attached to the head 14 of the muscle energy converter 10 and contraction pulls the piston 12 into the cylinder 16 thereby displacing fluid under pressure through the outlet port 20. The outlet port 20 communicates with the intra-aortic balloon pump 110 through a non-compliant conduit 112 filled with incompressible fluid so that the volume displaced from the converter 10 pushes a similar volume of fluid into the balloon pump 110 without delay. This pressurized fluid 79 may fill the balloon directly or activate a second piston which translates low-volume, high pressure hydraulics to a higher volume, lower pressure displacement more suitable for aortic counterpulsation. Muscle contraction is activated by a cardio-myostimulator 114 that monitors the heart and sends a burst of stimuli to the muscle so that contraction coincides with the diastolic phase of the cardiac cycle. In this way, fluid 79 inflates the balloon within the walls of the aorta and displaces blood such that cardiac afterload is reduced and coronary perfusion is increased. Following contraction, the balloon is deflated as the piston 12 is pushed from the cylinder 16 by the described axial preload magnetic forces and fluid 79 is drawn back towards the muscle energy converter 10.

b) extra-aortic counterpulsation pumps activated in the same manner as a) with the exception that the aorta is compressed from the outside via balloon inflation or pusher-plate actuation. This scheme employs no blood-contacting components, thereby avoiding complications due to thrombosis, hemolysis and balloon calcification. A balloon occluder device is disclosed in U.S. patent application Ser. No. 08/228,150, titled "Occluder Device and Method of Making", by John J. Pacella and Richard E. Clark, having attorney docket number AHS-3, filed the same day as the present application.

c) intra-ventricular balloon pumps activated in the same manner as a) with the exception that the balloon is placed within the ventricular cavity of the heart and inflated during the systolic portion of the cardiac cycle to increase cardiac output and reduce the work required of the native heart.

d) cardiac compression devices activated in the same manner as a) with the exception that the pressurized fluid 79 activates a hydraulic mechanism 110 external to the heart (e.g. pusher-plates, balloon patches, etc.) so that the ventricle(s) of the heart are compressed through direct displacement of the epicardium during the systolic portion of the cardiac cycle to increase cardiac output and reduce the work required of the native heart. This scheme employs no blood-contacting components, thereby avoiding complications due to thrombosis, hemolysis and balloon calcification.

e) positive displacement ventricular assist devices (left or right) activated in the same manner as a) with the exception that the pressurized fluid displaces a pusher-plate that in turn compresses a flexible blood-filled sack and expels blood from the pump during the systolic portion of the cardiac cycle.

f) positive displacement bi-ventricular assist devices and total artificial hearts—identical to e) with the exception that two blood pumps are activated simultaneously.

This invention may also be used in an assortment of other noncardiac applications such as:

g) actuation of hydraulic balloon occluder devices employing the same hydraulic actuation method described in a) with the exception that the device 110 inflates around some vessel or prosthetic conduit such that the lumen is collapsed and flow is restricted. Muscle contraction is activated with a myostimulator 114 triggered automatically by some event (e.g. motor failure of an implanted centrifugal pump) or manually by placing a magnet over the myostimulator 114 (e.g. for use as an artificial sphincter).

h) voluntary muscular actuation of prosthetic limbs employing the same hydraulic actuation method described in a) with the exception that the target device 110 comprises a hydraulic piston connected across the joint of a prosthetic limb (e.g. artificial elbow, hand, knee, etc.). In this manner, the limb is activated by the voluntary contraction and relaxation of the muscle attached to the muscle energy converter 10.

i) hydraulic displacement of the diaphragm (or some replacement prosthesis) to aid in respiration employing the same hydraulic actuation method described in a) with the exception that the target device 110 (e.g. a piston) displaces the diaphragm (or replacement prosthesis) downward so that intrathoracic pressure is reduced and inspiration ensues. Expiration may also be aided by the active removal of fluid from the diaphragm piston by the magnetic bearing of the muscle energy converter 10. Muscle contraction and subsequent muscle energy converter compression is activated by a myostimulator 114 which can be triggered by impulses received from the phrenic nerve or pre-programmed in a control means 116 to deliver burst stimuli at a certain rate.

j) augmentation of lymphatic flow via hydraulic compression of large lymphatic vessels employing the same hydraulic actuation method described in a) with the exception that the target device 110 (e.g. a fluid-filled balloon) periodically squeezes a major lymphatic duct such that its contents are expelled, thereby increasing lymphatic flow. Muscle contraction and subsequent muscle energy converter 10 compression can be activated by a myostimulator 114 pre-programmed to deliver burst stimuli at a certain rate by control means 116.

Figure 10A:
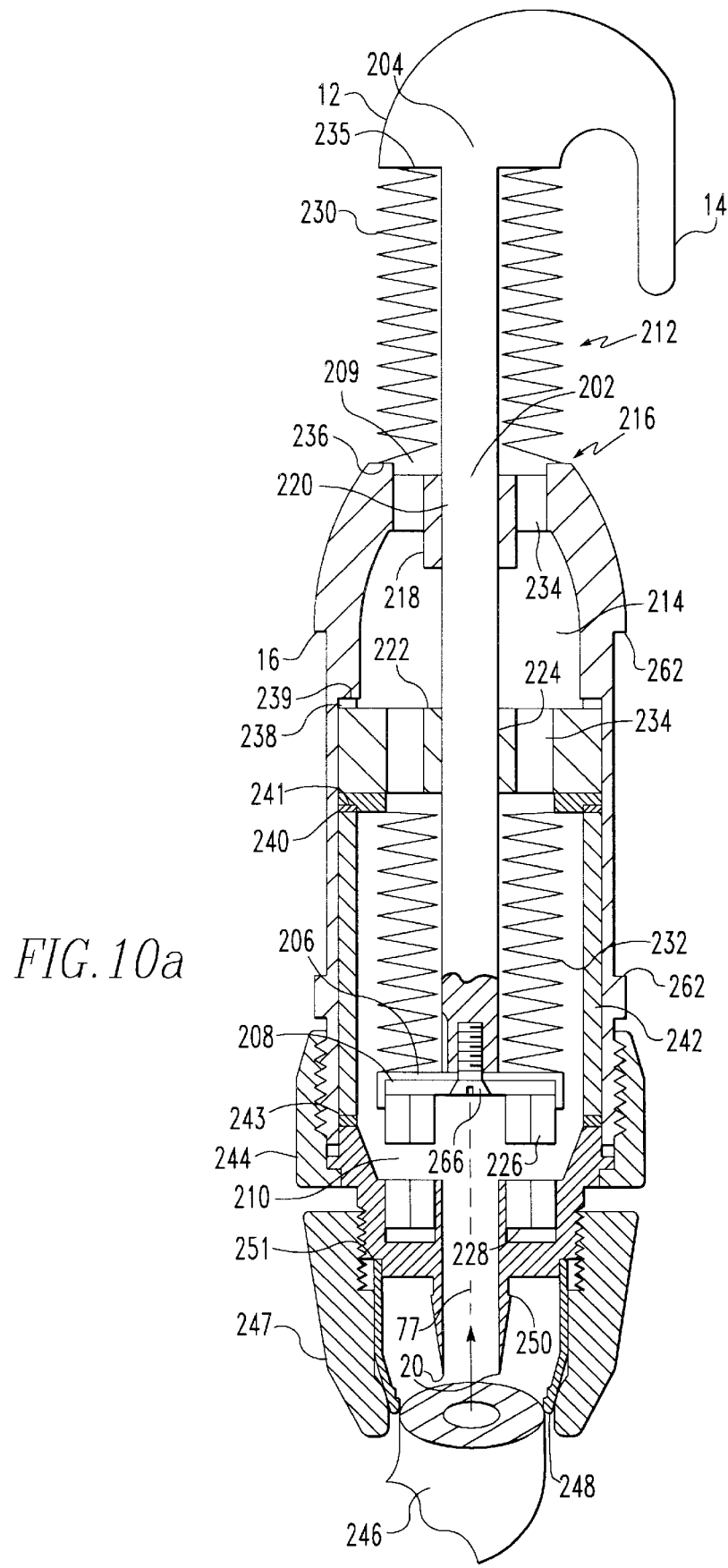
FIG. 10a is a schematic representation of a cross-sectional view of another embodiment of the muscle energy converter.

Referring to FIG. 10a thereof, there is shown an alternative embodiment of a muscle energy converter 10 for pumping fluid, such as blood, in a patient. The muscle energy converter 10 comprises a piston 12, as shown in FIG. 10i and 10j, having an attachment head 14 which connects to tissue, preferably muscle 13. The piston 12 also has an elongate portion 202 having a first end 204 and a second end 206. The first end 204 is connected to the attachment head 14. The piston 12 has a base 208 connected to the second end 206. The muscle energy converter 10 also comprises a housing, such as a cylinder 16, having a chamber 18. The cylinder 16 has a piston port 209 in communication with the chamber 18 and an output port 20 in communication with the chamber 18. The base 208 is disposed in the chamber 18 of the cylinder 16 with the elongate portion 202 extending from the base 208 through the piston port 209. The base 208 and the cylinder 16 define a fluid cavity 210 in the chamber 18 in which fluid to be pumped by the piston 12 is disposed. The muscle energy converter 10 is also comprised of an expandable seal to position about the piston 12 for defining a pumping cavity 214 in which the piston 12 moves. The expandable seal 212 prevents fluid from entering the pumping cavity 214.

The cylinder 16 preferably includes a guide mechanism 216 for guiding the piston 12 in its movement. The guide mechanism 216 is in communication with the piston 12 and the cylinder 16. Preferably, the guide mechanism 216 includes a first bushing 218 connected to the cylinder 16 at the piston port 209. The first bushing 218 has a first opening 220 through which the elongate portion 202 extends. The guide mechanism 216 preferably includes a second bushing 222 disposed in and connected to the cylinder 16. The second bushing 222 has a second opening 224 through which the elongate portion extends. The base 208 is disposed between the second bushing 222 and the outlet port 20.

The piston 12 preferably has at least a first magnet 226. Preferably, the cylinder 16 has at least a second magnet 228 in opposition to the first magnet 226 such that the closer the first magnet 226 and second magnet 228 become, a greater a repulsive force is created between them. The first magnet 226 is preferably disposed on the base 208 and the second magnet 228 is disposed on the cylinder 16 adjacent the output port 20 and opposing the first magnet 226 on the base.

The expandable seal 212 preferably includes an outer bellow 230 connected to the attachment head 14 and the cylinder 16 about the piston port 209 such that the elongate portion 202 that extends out of the cylinder 16 through the piston port 209 is disposed in the outer bellow 230 and no fluid outside the outer bellow 230 is able to get between the elongate portion 202 and the outer bellow 230 and into the cylinder 16. The expandable seal 212 preferably includes an inner bellow 232 connected to the base 208 and the second bushing 222 such that the elongate portion 202 extending past the second bushing 222 toward the outlet port 20 is disposed in the inner bellow 232 and no fluid outside of the inner bellow 232 can get between the inner bellow 232 and the elongate portion 202. Preferably, the first and second bushing each has at least one fluid vent 234 to allow fluid in between the respective bellow and the elongate portion 202 to flow through the respective bushings as the piston 12 moves relative to the housing.

The present invention pertains to a method for pumping fluid in a patient. The method comprises the steps of attaching an attachment head 14 of a piston 12 to tissue, such as a muscle 13, of the patient. Next, there is the step of placing a housing, such as a cylinder 16, to the patient's body. The piston 12 is disposed in and extending from the housing. The placing step preferably includes the step of fixing the cylinder 16 to the ribs 72 of the patient with the outlet port 20 located distally. The attaching step preferably includes the step of attaching the piston attachment head 14 to the proximal tendon 21 of the latissimus dorsi muscle 71 with the cylinder 16 having its long axis 77 aligned with the primary force vector of the latissimus dorsi muscle 71.

Then, there is the step of introducing fluid into a fluid cavity 210 of the cylinder 16. Next, there is the step of moving the piston 12 with the muscle 13 of the patient connected to the piston attachment head 14 so the fluid in the fluid cavity 210 is pumped out of the fluid cavity 210 by a base 208 of the piston 12 pushing fluid out of the fluid cavity 210.

The moving step preferably includes the step of reconfiguring a pump cavity 214 in which the piston 12 moves to pump the fluid in the fluid cavity 210 as the muscle 13 moves. The reconfiguring step preferably includes the steps of constricting an outer bellow 230 connected between the cylinder 16 and the piston attachment head 14 while expanding an inner bellow 232 connected between the base 208 of the piston 12 and a first bushing 218 to pump the fluid out of the fluid cavity 210. Next, there is the step of expanding the outer bellow 230 while constricting the inner bellow 232 to allow the fluid cavity 210 to fill with fluid. Preferably, the moving step includes after the constricting step, the step of increasing a repulsive force between the base 208 of the piston 12 and an output port 20 of the cylinder 16 as the base 208 and the outlet port 20 come closer together.

The present invention pertains to a muscle energy converter 10. The muscle energy converter 10 comprises a piston 12 having an attachment head 14 for connection to tissue of a patient. The muscle energy converter 10 also comprises a cylinder 16 having a chamber 18, in which the piston 12 is disposed. The cylinder 16 has an outlet port 20 for transport of fluid in the chamber 18 as the tissue moves the piston 12. Additionally, the muscle energy converter 10 comprises a mechanism 211 for securing the cylinder 16 to the patient, as shown in figures 11a and 11b.

The present invention pertains to a method of using muscle energy. The method comprises the steps of attaching a muscle 13 of a patient to an attachment head 14 of a piston 12. Next there is the step of securing the cylinder 16 to the 30 body of the patient. Then, there is the step of moving with the muscle 13 the piston 12 within the surrounding cylinder to pressurize fluid within the cylinder 16.

In the operation of the preferred embodiment, the assembly of the muscle energy converter 10, shown in FIG. 10a, is as follows.

Figure 10B:
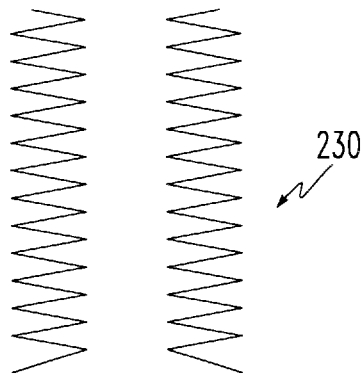
FIG 10b is a schematic representation of the outer bellows.
Figure 10D:
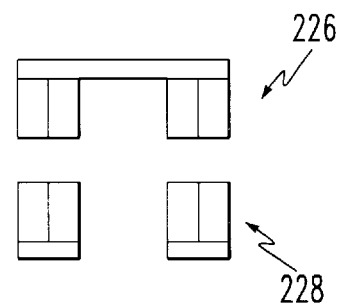
FIG. 10d is a schematic representation of the first and second magnets.
Figure 10C:
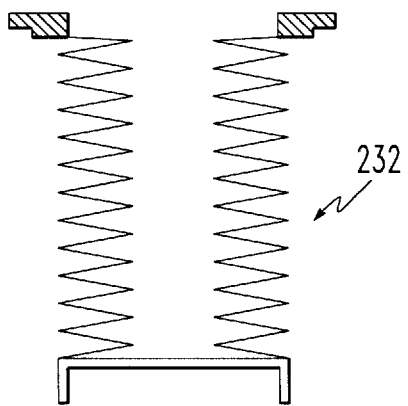
FIG. 10c is a schematic representation of the inner bellows.
Figure 10E:
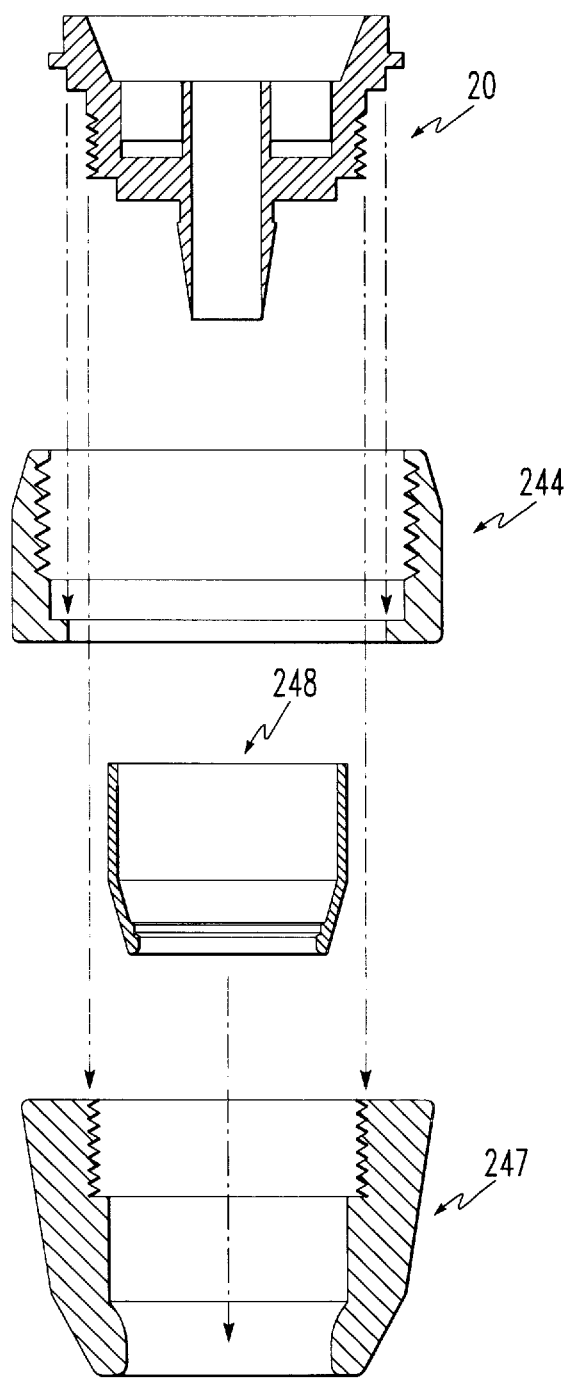
FIG. 10e is a schematic representation of the output port with various collets.
Figure 10G:
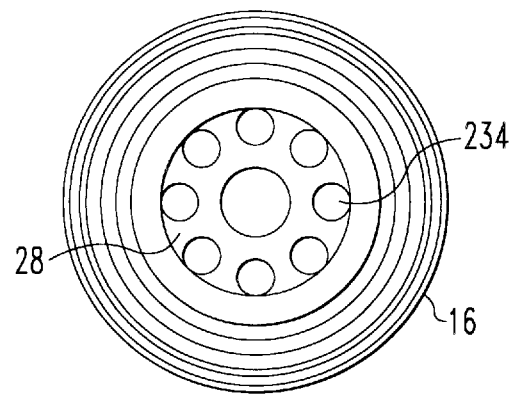
FIG. 10g is a schematic representation of a top view of the housing with bushings.
Figure 10F:
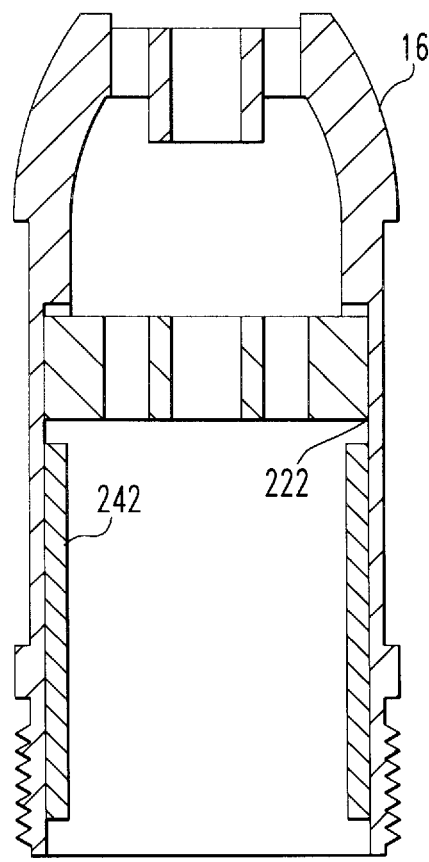
FIG. 10f is a schematic representation of a side view of the housing with bushings and support cylinder.

1. slide the outer bellows 230, as shown in FIG. 10b, over the elongate portion 202 until it contacts the ledge 235 formed by the piston attachment head 14;
2. weld the terminal convolution of the outer bellows 230 to the piston attachment head 14 along its entire circumference (to hermetically seal the joint);
3. slide the elongate portion 202 into the cylinder housing 16 through first bushing 218 until the outer bellows 230 contacts the top 236 of the housing 16;
4. weld the remaining terminal convolution of the outer bellows 230 to the cylinder housing 16 along its entire circumference (to hermetically seal the joint);
5. place the first o-ring 238 over the inner ridge 239 of the cylinder housing 16;
6. slide second bushing 222 into the cylinder housing 16 and around the elongate portion 202 so that it rests against the first o-ring 238;
7. slide the inner bellows 232, as shown in FIG. 10c, into the cylinder housing 16 (stationary end first) until it contacts second bushing 222;
8. place the first magnet 226 into the recess of the inner bellows' terminal fitting the base 208 (steel pole piece first);
9. screw the first magnet 226, as shown in FIG. 10d, inner bellows 232 and elongate portion 202 together applying silicone rubber around the central aperture to ensure a water-tight seal;
10. place the second o-ring 240 in the groove 241 formed by the inner bellows' stationary fitting and the cylinder housing inner wall;
11. slide the support cylinder 242, as shown in FIG. 10f, into the cylinder housing 16 so that it rests against the second o-ring 240;
12. place the second magnet 228 into the recess of the outlet port 20 (steel pole piece first) and secure with silicone adhesive;
13. place the third o-ring 243 over the end of the support cylinder 242 (inside the cylinder housing 16);
14. slide the outlet port 20, shown in FIG. 10e, into the cylinder housing 16 until it contacts the third o-ring 243;
15. place the first collet 244 over the outlet port 20 and secure to the cylinder housing 16 by screwing the first collet 244 onto the threads of the cylinder housing 16;
16. tighten the first collet 244 so that the internal cylinder components (second bushing 222; inner bellows 232; support cylinder 242; and all 3 o-rings) are compressed between the cylinder housing 16 and outlet port 20.

To attach conduit 246 (tubing) to outlet port 20:
1. slide the second collet 247 over the conduit 246 with the threaded side positioned toward the muscle energy converter 10-end of the conduit 246;
2. slide the tined ferrule 248 over the conduit 246 with the tines facing away from the muscle energy converter 10-end of the conduit 246 (the tined ferrule 248 will be between the second collet 247 and the end of the conduit 246);
3. push the conduit 246 over the barbs 250 of the outlet port 20 until it contacts the main body of the port 20;
4. slide the tined ferrule 248 into the lower ledge 251 of the outlet port 20;
5. slide the second collet 247 against the external threads of the outlet port 20 and secure by screwing the second collet 247 onto the outlet port 20 until a tight fit is achieved (at this point, the conduit 246 will be held into place by the outlet port barbs 250 and the tines of the tined ferrule 248 which are being compressed against the conduit wall by the second collet 247).

The tined ferrule 248 is placed over the conduit 246 (tubing) to protect it from being twisted while the second collet 247 is screwed into place. It also serves to prevent the conduit 246 from slipping off the outlet port 20 by gripping into the tubing wall with its terminal barbs (like a fishhook). Note that the barbs are pushed toward the center of the conduit 246 as the second collet 247 is tightened—this is made possible by eight vertical slots machined into the tined ferrule 248.

The muscle energy converter 10 is anchored beneath the proximal portion of the latissimus dorsi muscle 71 via two titanium plates 260 which secure the muscle energy converter 10 to the ribcage 73, as shown in FIGS. 11a and 11b. A wide depression 262 in the cylinder housing 16, extending around its entire circumference, provides means to attach the pair of anchor plates 260 to the muscle energy converter 10. These rounded plates 260 fit snugly within the depression 262 and extend to either side of the muscle energy converter 10 like the wings of a biplane. The plates 260 are screwed to the cylinder wall along the top of the depression 262 where the wall is thickest. The muscle energy converter 10 is seated within the plane of the ribcage 73 by resecting 2–3 ribs so that the muscle energy converter 10 housing 16 fits within the gap. The muscle energy converter 10 is then secured to the ribcage 73 by placing the free ribs 72 between the plates 260 and screwing the plates 260 and ribs 72 together, as shown in FIGS. 11a and 11b.

The outer bellows 230 is edge-welded directly to the titanium housing 16 at one end and to the piston attachment head 14 at the other. The base of the inner bellows 232 is compressed between the second bushing 222 and the support cylinder and is sealed with a second nylon o-ring 240. The mobile end of the inner bellows 232 is attached to the piston 12 at its base 208 via a central screw 266. This screw 266 has an o-ring seal (not shown) to prevent fluid from entering the pumping cavity 214.

The spring constant of the bellows is about 3.78 N/cm each (1N=0.225 lbs). This means that the outer bellows 230 should be heat-treated at a length of 58.5 mm in order to provide the recoil force necessary to stretch the muscle (roughly 5N or 1.13 lbs) at full piston extension. Note that at full extension, the outer bellows 230 should be pulling the piston 12 OUT with a force of 8.8N and the inner bellows 232 should be pushing the piston 12 IN with a force of 3.8N (yielding a net force of 5N OUT).

The bellows physical properties looks like this:

Outer Bellows 230:

| | |
|---|---|
| OD = | 0.620" |
| ID = | 0.234" |
| Thickness = | 0.002" |
| Material = | Titanium (15-3-3-3) |
| # of convolutions = | 60 |
| Die # = | DD-464 |
| Heat-treat Length = | 2.303" (.023 pitch)* (*see below) |
| Compressed Length = | 0.992" |

Fittings: Weld to customer supplied fittings

-continued

The bellows physical properties looks like this:

Inner Bellows 232:

| | |
|---|---|
| OD = | 0.620" |
| ID = | 0.234" |
| Thickness = | 0.002" |
| Material = | Titanium (15-3-3-3) |
| # of convolutions = | 60 |
| Die # = | DD-464 |
| Heat-treat Length = | 0.866" (0.14 pitch) |
| Compressed Length = | 0.472" - fully collapsed |
| Fittings: Senior Flexonics supplies fittings and welds bellows to these fittings (fitting material = A-40 Titanium). | |

Moreover, the pitch of the outer bellows should be as large as possible to minimize problems due to tissue infiltration.

The tubing 246 which attaches to the outlet port 20 of the muscle energy converter 10 acts as a simple non-compliant conduit through which fluid is free to move. This conduit 246 will be filled with the transmission fluid of choice (water, saline, silicone oil, etc.) so that translation of the piston 12 will displace said fluid into the tubing 246 causing an instantaneous shift in volume from one end of the conduit 246 to the other (due to the incompressible nature of the fluid). The displaced fluid will enter the actuator of the target device causing it to perform the work for which it was designed (e.g. pumping blood). During muscle relaxation, the fluid balance will return to its original state, shifting from the target device to the muscle energy converter 10. No valves or other components are added to the fluid path—its simply a clear channel from one device to another.

The muscle energy converter 10 is designed to operate in synchrony with the heart (during partial cardiac assist) and must therefore match the heart rate. This is typically 72 beats per minute (bpm) at rest, increasing to as much as 140 bpm during heavy exercise. However, in practice, muscle energy converter 10 actuation rates are set to some maximum (say 60 bpm) so that when the heart rate increases above that level, the assist ratio will drop to keep muscle energy converter 10 actuation below that preset limit (thus serving to protect the muscle from overuse and ensure adequate time for pump filling between contractions).

If the muscle energy converter 10 were used to drive a total artificial heart, the pumping rate would be set independent of the native heart at whatever rate is necessary to maintain adequate perfusion. This rate will depend heavily on the design of the blood pump (e.g. stroke volume, etc.)

The output characteristics of the muscle energy converter 10 are directly governed by the contractile properties of the latissimus dorsi muscle. However, the timing and duration of these contractions are ultimately dictated by an implanted myostimulator which senses cardiac depolarization and responds by delivering a rapid succession of pulses to the muscle nerve. These commercial stimulators are fully programmable via transcutaneous telemetry and provide a wide variety of stimulation and synchronization programs (including non-synchronous modes). As a result, stimulation programs can be easily modified to alter latissimus dorsi dynamics and control muscle energy converter 10 function. For instance, contractile strength can be altered by changing the number of pulses per burst while muscle activation time is controlled by modifying the duration of the burst. The number of muscle energy converter 10 compressions per minute can also be controlled by programming a set rate into the stimulator or, in the case of cardiosynchronous operation, by setting the heart beat-to-muscle contraction ratio.

Figure 10H:
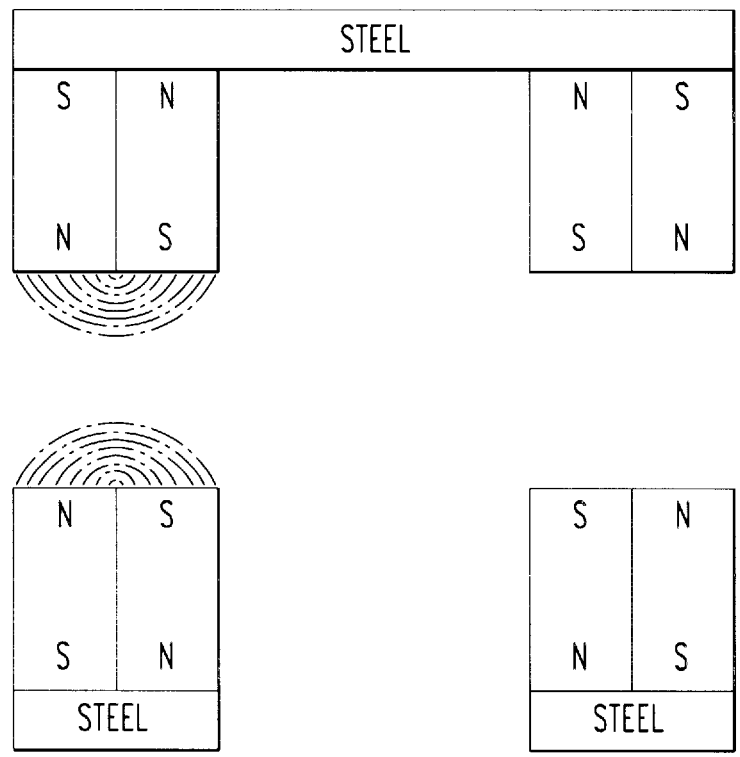
FIG. 10h is a schematic representation of a multi pole configuration of the first and second magnets.

The muscle energy converter activation sequence is the following:

1. the myostimulator senses cardiac event or determines via an internal timer that a burst stimulus is required;
2. the myostimulator sends a train of pulses to the muscle nerve;
3. the muscle contracts in response to the burst stimuli and pulls the piston 12 into the muscle energy converter 10 housing 16;
4. the elongate portion 202 slides inward past the two bushings causing
    a. the outer bellows 230 to compress;
    b. the inner bellows 232 to expand;
    c. air to move from the outer bellows 230 into the inner bellows 232 via the vents 234, as shown in FIG. 10g, which surround both bushings;
    d. fluid to be expelled from the housing 16 into the conduit 246; and
    e. fluid to enter the actuator of the target device causing motion.
5. elongate portion 202 motion continues until:
    a. muscle contraction ceases;
    b. the piston 12 reaches the end of its stroke whereupon the magnetic stroke limiter comprised of the first and second magnets, as shown in FIG. 10h, counteracts the force of the muscle;
6. the muscle stops contracting and begins to relax;
7. the combined spring force of the bellows (and the magnetic force of the stroke limiter in the case of full muscle energy converter 10 compression) serve to extend the piston 12 out from the muscle energy converter 10 housing 16;
8. the elongate portion 202 slides outward past the two bushings causing
    a. the outer bellows 230 to expand;
    b. the inner bellows 232 to compress;
    c. air to move from the inner bellows 232 into the outer bellows 230 via the vents 234 which surround both bushings;
    d. fluid to be pulled into the housing 16 from the conduit 246; and
    e. fluid to evacuate the actuator of the target device causing reverse motion.
9. elongate portion 202 motion continues until the piston 12 reaches the end of its stroke whereupon the inner bellows 232 completely collapses and stops piston 12 extension;
10. repeat step #1.

Figure 12:
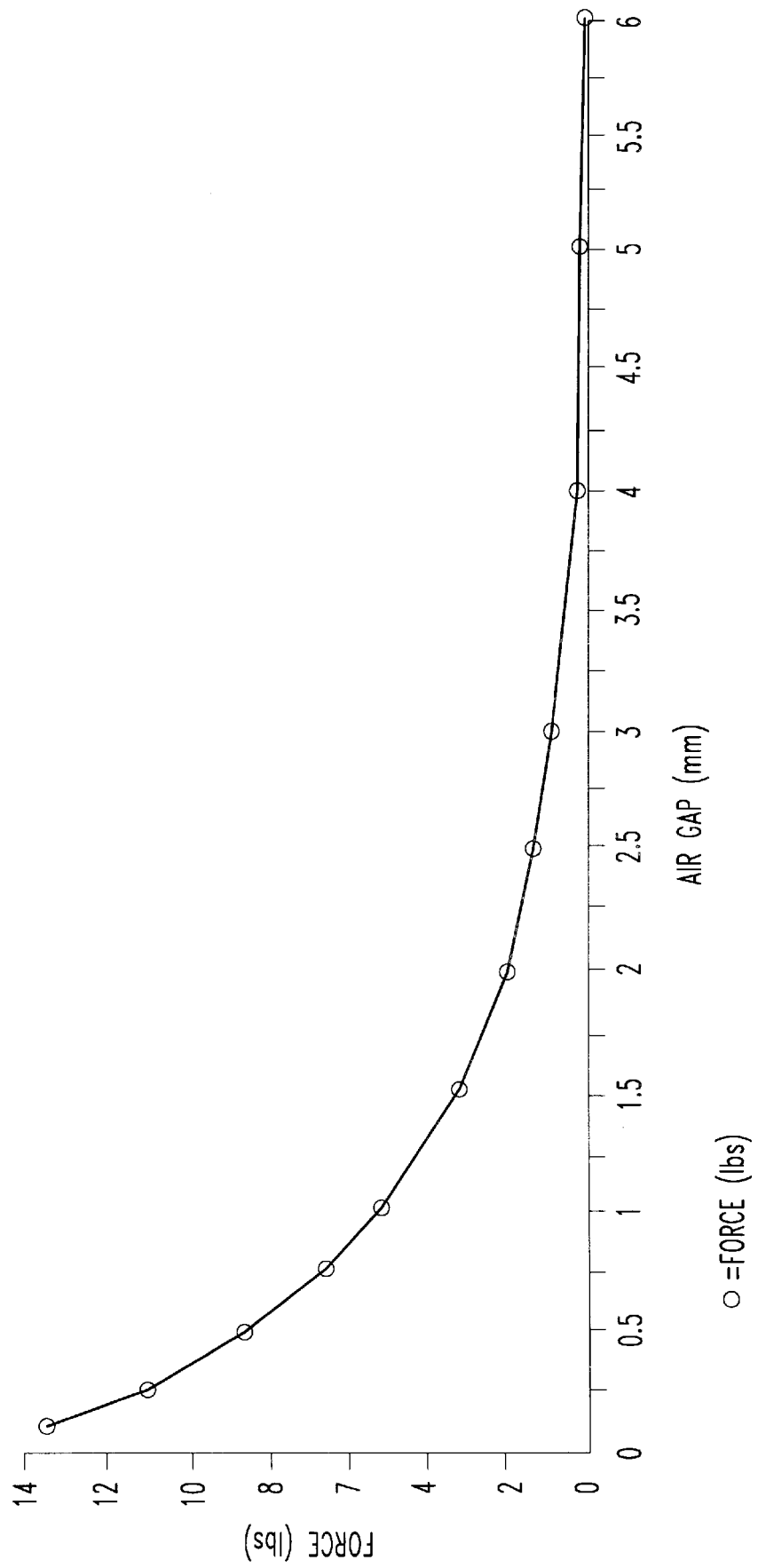
FIG. 12 is a graph of force versus gap in regard to a multipole design for the first and second magnets.

FIG. 12 shows a graph of force vs. gap in regard to the first and second magnets.

Analysis of Repulsive Forces Between MEC Magnets as a Function of Separation

Dimensions

Magnet #1 0.574"O.D.×0.252"I.D.×0.157"Tk Mag'd 2 Poles one Face thru Tk

Material Neo 45 MGOe

Steel Pole Piece for Magnet #1; same O.D. & I.D.×0.050"Tk

Magnet #2 0.574"O.D.×0.252"I.D.×0.157"Tk Mag'd 2 Poles one Face thru Tk

Material Neo 45 MGOe

Steel Pole Piece for Magnet #2; same O.D. & I.D.×0.050"Tk

| Air Gap (mm) | Force (Lbs) |
|---|---|
| 0.10 | 13.4 |
| 0.25 | 11.0 |

-continued

| Air Gap (mm) | Force (Lbs) |
|---|---|
| 0.50 | 8.5 |
| 0.75 | 6.6 |
| 1.00 | 5.1 |
| 1.50 | 3.2 |
| 2.00 | 2.1 |
| 2.50 | 1.4 |
| 3.00 | 1.0 |
| 4.00 | 0.5 |
| 5.00 | 0.3 |
| 6.00 | 0.2 |

Figure 13:
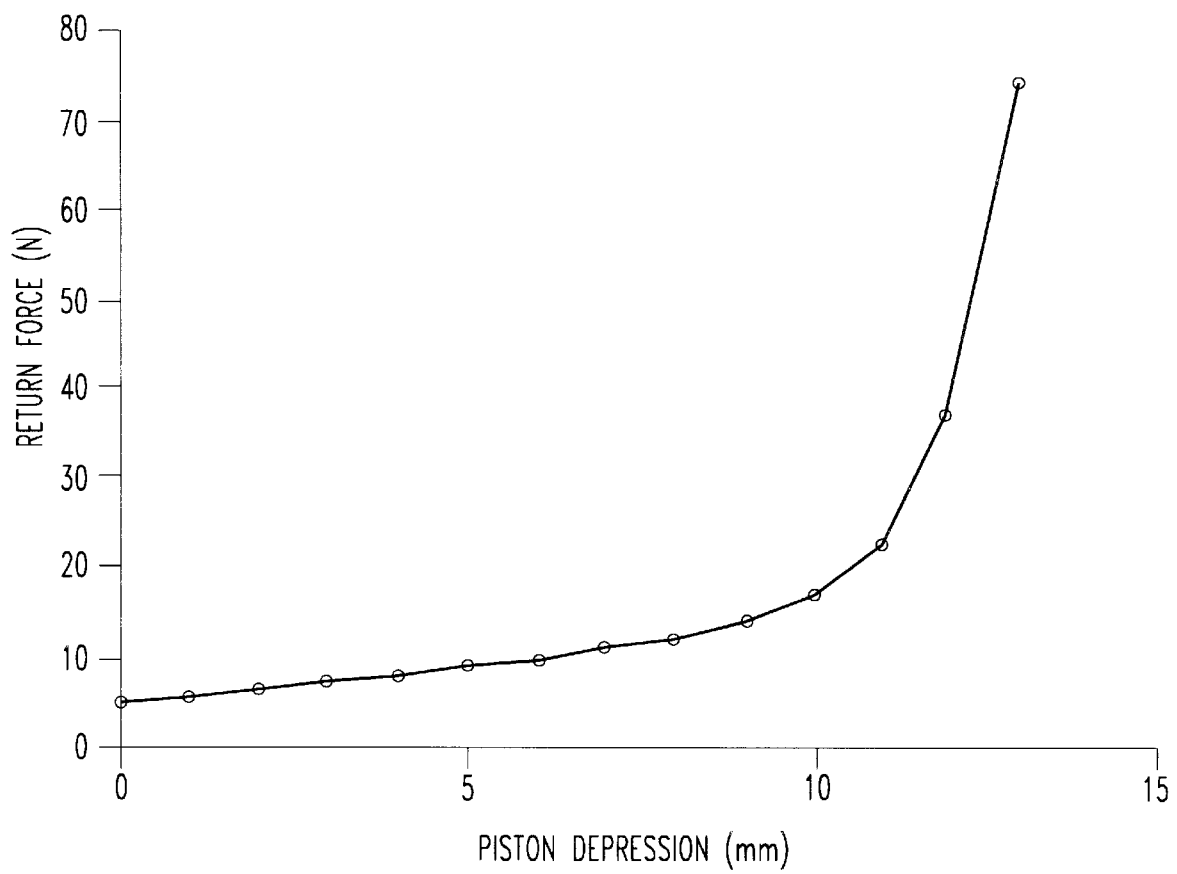
FIG. 13 is a graph of the expected return force of the piston as a function of piston position within the housing.

The graph of FIG. 13 depicts the expected return force of the piston as a function of piston position within the MEC housing (zero piston depression corresponding to full outward extension). These forces are a combination of the bellows' linear spring effect (dominant from 0–10 mm piston depression) and the repulsive forces of the magnets (dominant from 11–13 mm piston depression).

Note: A minimum return force of 5N was chosen based on data collected from in vivo, trained skeletal muscle. These data show the average resting tension of these muscles to be 3.5N.

Figure 14:
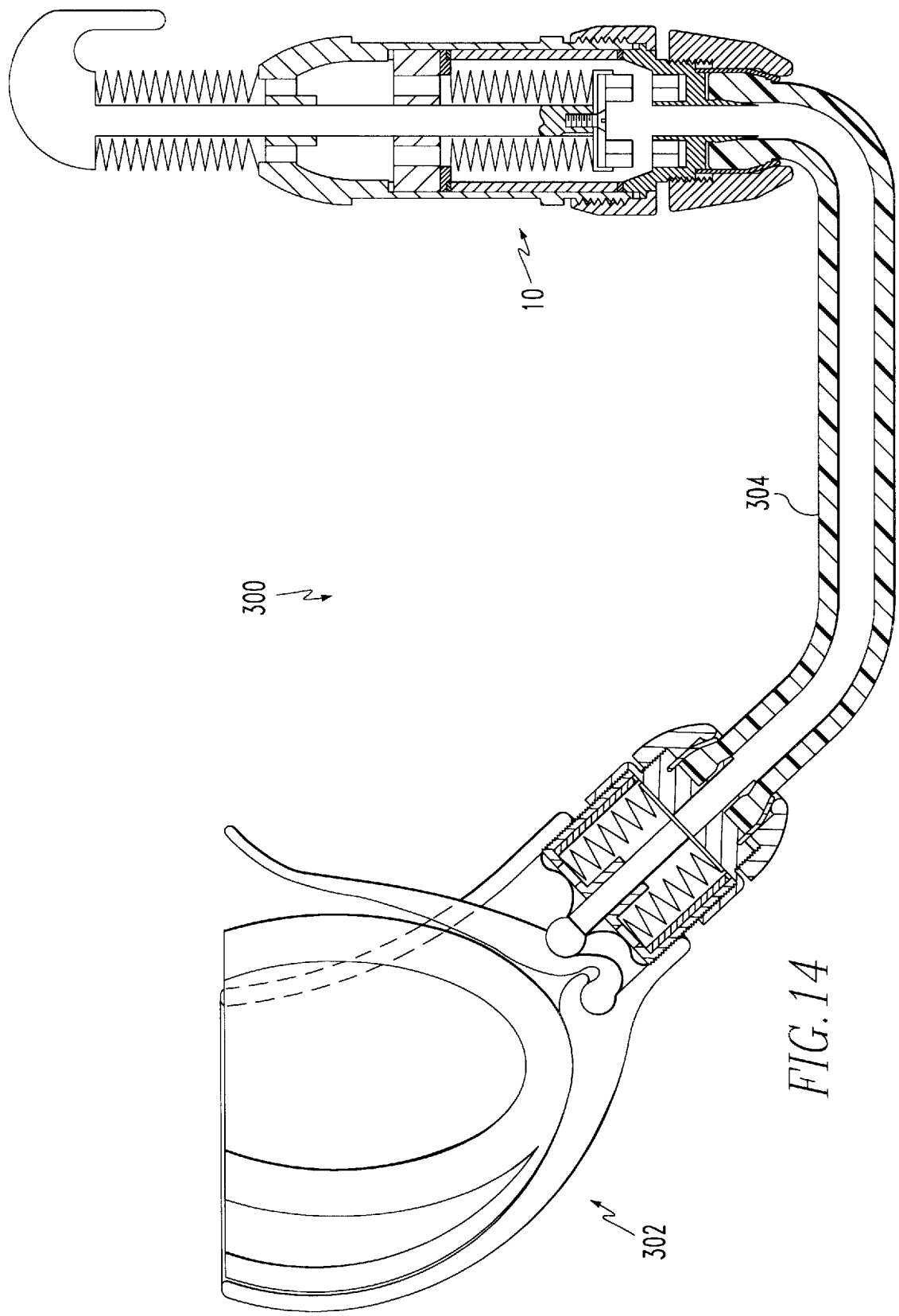
FIG. 14 is a schematic representation of a muscle energy converter ventricular assist system of the present invention.

The present invention pertains to a system 300 for assisting the operation of a patient's heart 342, as shown in FIG. 14. The system 300 comprises a muscle energy converter 10 which is capable of connecting to a muscle of the patient for converting energy of the muscle into a mechanical force. The system 300 also comprises a ventricular assist device 302 connected to the muscle energy converter 10 for receiving the mechanical force from the muscle energy converter 10 and compressing the heart 342 of the patient. The assist device 302 is capable of connection and operational engagement with the heart 342.

Figure 15:
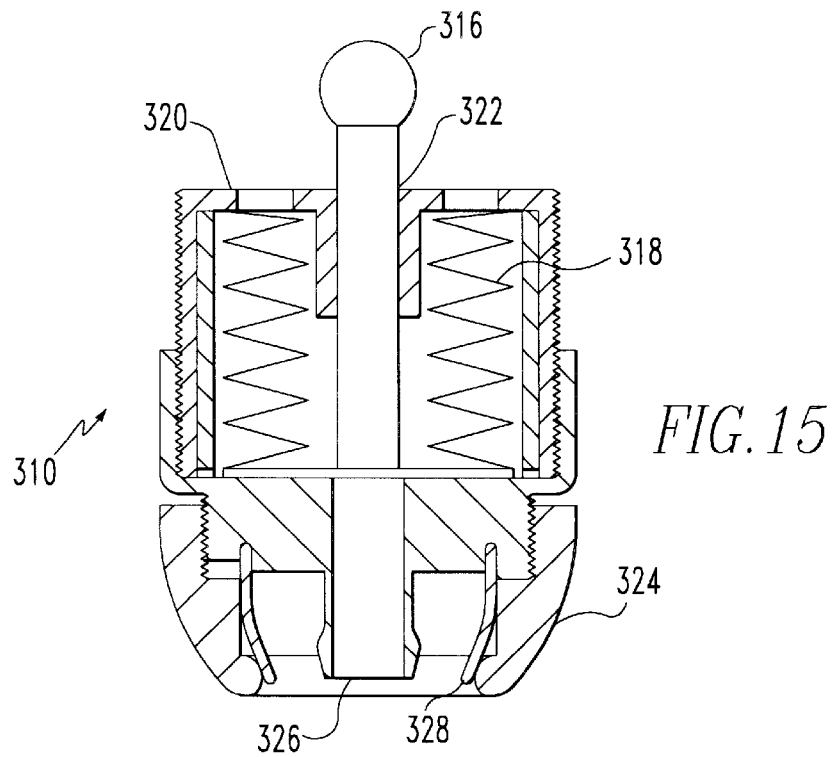
FIG. 15 is a schematic representation of an actuator of the assist device of the present invention.
Figure 16:
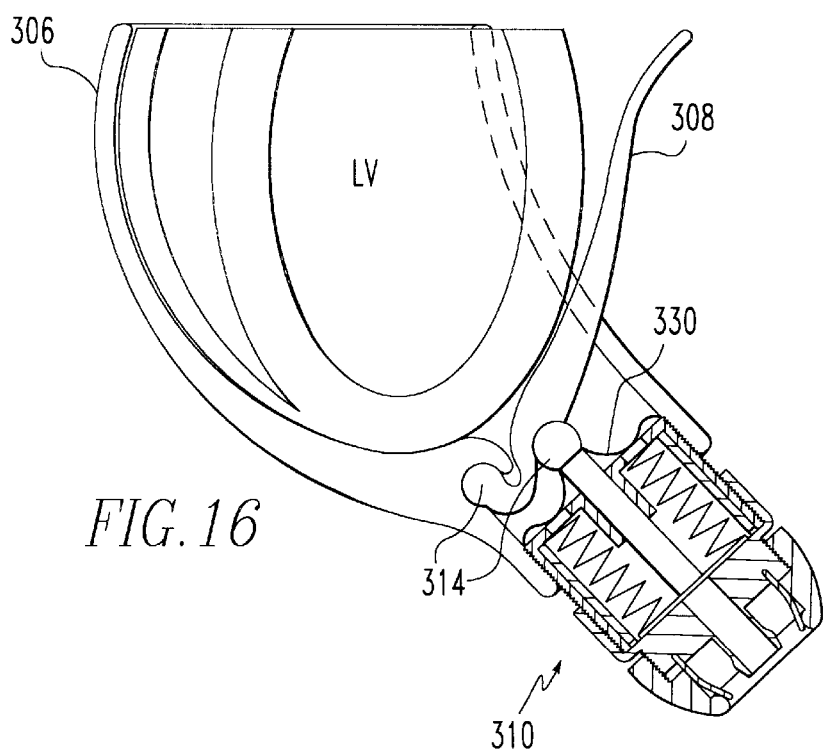
FIG. 16 is a schematic representation of the assist device.
Figure 20:
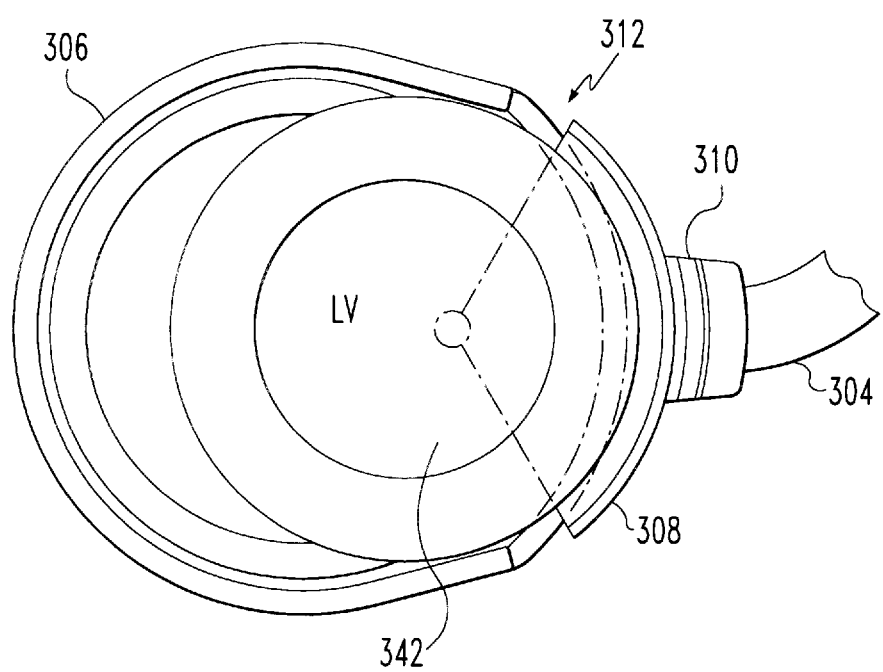
FIG. 20 is a schematic representation of an overhead view of the hydraulic ventricular assist device.
Figure 22:
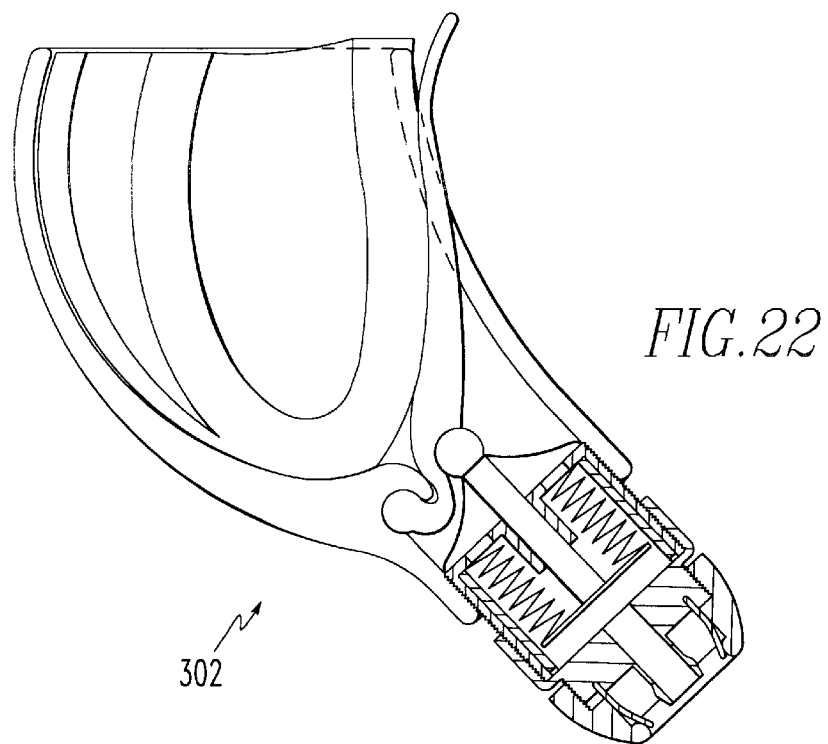
FIG. 22 is a schematic representation of the assist device in a fully compressed position.

Preferably the assist device 302 includes a conduit 304, as shown in FIG. 20, connected to the muscle energy converter 10. Additionally, the assist device 302 comprises fluid which is forced, and preferably pumped by the muscle energy converter 10 through the conduit 304 to the assist device 302 where the fluid causes the assist device 302 to compress the heart 342, as shown in FIG. 22. The assist device 302 preferably also comprises a shell 306 which fits about the heart 342. The assist device 302 preferably comprises a compression plate 308 which pivotably connects with the shell 306. Additionally, the assist device 302 preferably comprises an actuator 310, as shown in FIG. 15, which is connected to the conduit 304 and receives the fluid which causes the actuator 310 to press against the plate 308 and pivots the plate 308 against the heart 342 in the shell 306.

The shell 306 preferably has an open face 312 through which the plate 308 pushes against the heart 342. Preferably, the plate 308 forms a ball and socket connection 314 with the shell 306. The actuator 310 preferably comprises an assist piston 316 which presses against the plate 308, forcing the plate 308 against the heart 342. The actuator 310 preferably includes bellows 318 in which the assist piston 316 is housed. The bellows 318 is compressed by the fluid pumped by the muscle energy converter 10 which in turn pushes the assist piston 316 against the plate 308.

Figure 21:
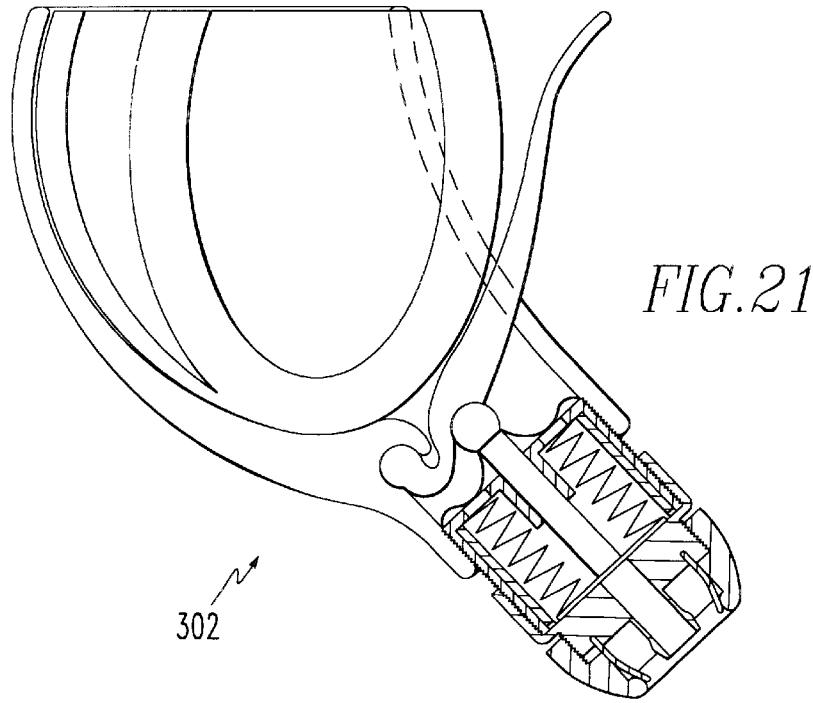
FIG. 21 is a schematic representation of the assist device in a fully open position.

The present invention pertains to a method for assisting the operation of a patient's heart 342. The method comprises the steps of converting energy from a muscle to a mechanical force with a muscle energy converter 10. Then there is the step of compressing the heart 342 of the patient with an assist device 302 with the mechanical force from the muscle energy converter 10, as shown in FIGS. 21 and 22.

Figure 18:
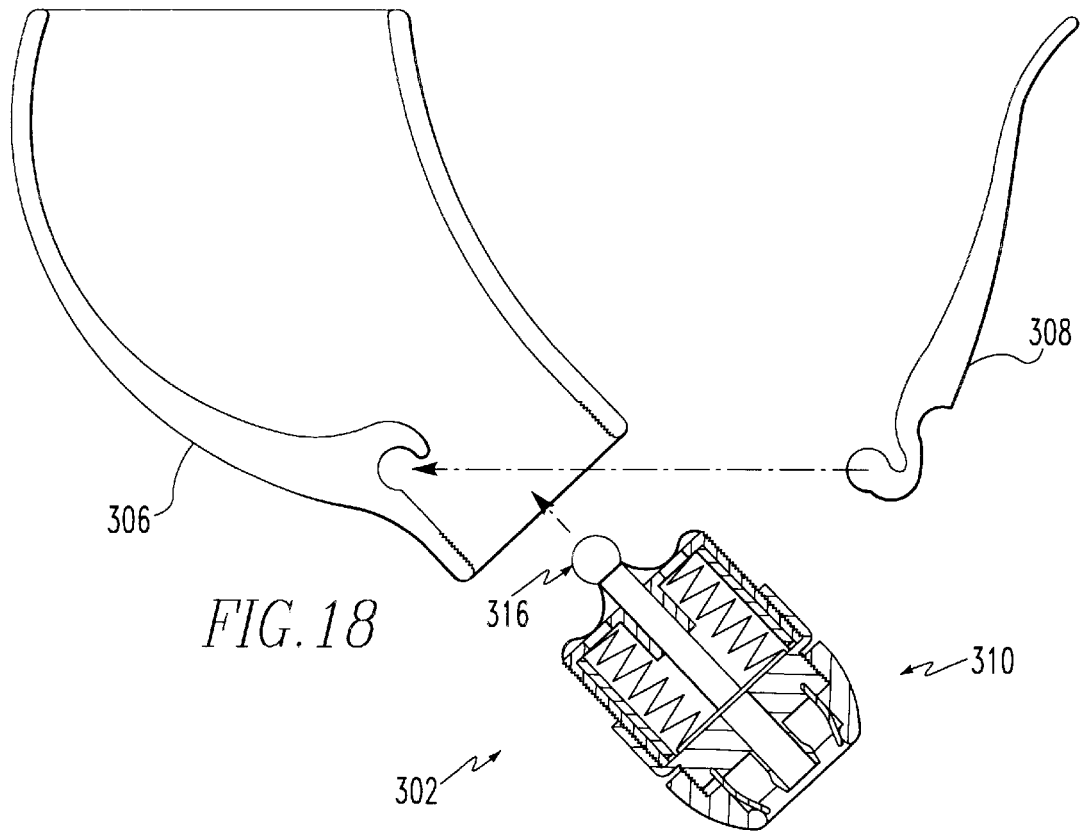
FIG. 18 is a schematic representation of the structural components of the assist device.
Figure 17:
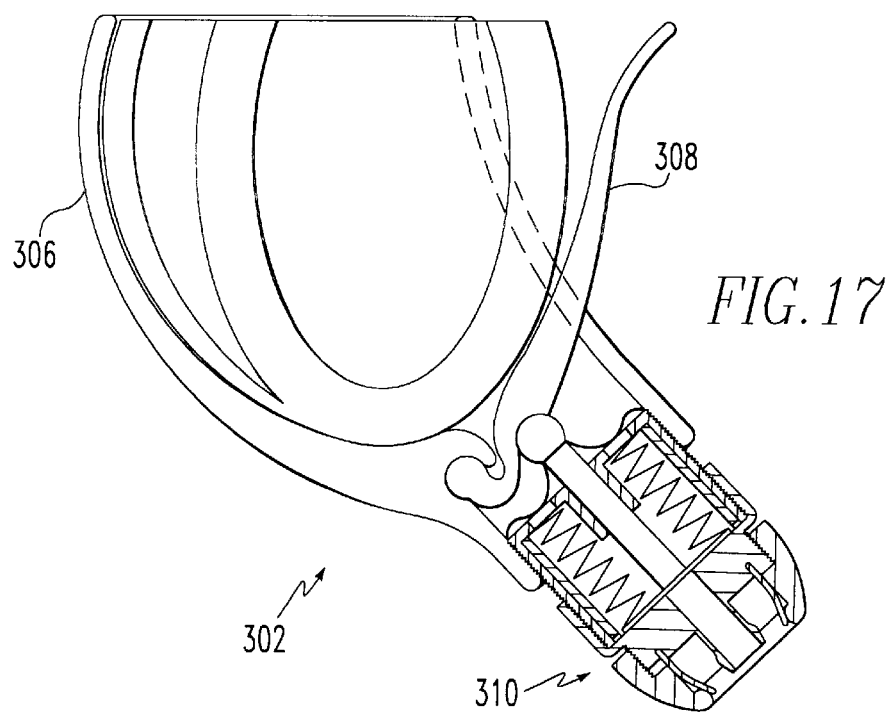
FIG. 17 is a schematic representation of the assist device.
Figure 19:
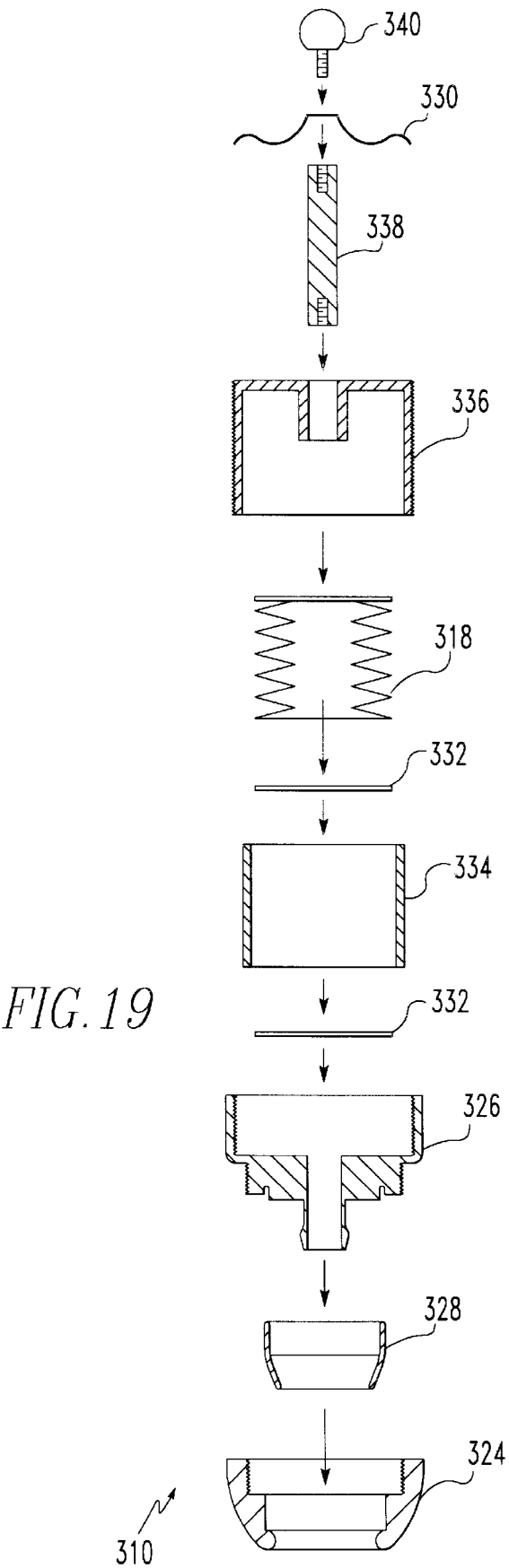
FIG. 19 is a schematic representation of the actuator components.

The hydraulic ventricular assist device 302 comprises three main components: a levered ventricular compression plate 308; a rigid pericardial housing 306; and a hydraulic actuator 310 (see FIGS. 17 and 18). The titanium compression plate 308 assumes a wedge (i.e., fan) shape with its tip near the apex of the heart 342. The plate 308 rotates about a ball-and-socket joint (the fulcrum) formed between the plate 308's apex (ball) and the rigid housing (socket). Force is applied to the plate 308 a short distance from its center of rotation via the spherical head of the actuator 310, which contacts the plate 308 in a ball-and-socket configuration (note: these joints are modelled after hip prostheses which have demonstrated excellent durability under chronic implant conditions). This assist piston 316 shaft is aligned to provide smooth rotation of the plate 308's socket about the spherical assist piston 316 head as it extends linearly. The assist piston 316 base is attached to a metal bellows 318 which responds to the pressures generated via the muscle energy converter 10 (or some other pressure source), as shown in FIG. 19. The assist piston shaft 338 is guided by a bushing located on the low-pressure side of the bellows 318. This bearing surface is shielded from biological infiltration by an assist flexible diaphragm 330 located between the cylinder housing and assist piston shaft 338. This diaphragm also serves to seal the actuator 310 so that lubricant can be introduced between it and the bellows 318 to maintain smooth bearing operation. Vents 320 are located around the periphery of the assist piston shaft 338 to allow lubricant to leave the bellows 318 chamber during compression and return during extension (i.e., for volume compensation). The actuator 310 is attached by screwing it into the pericardial housing.

The assist device 302 is activated when fluid from the energy source (e.g., MEC) enters the actuator 310 under high pressure (200 psig) and extends the assist piston 316 from its housing. The assist piston 316, in turn, supplies a torque to the lever arm producing rotation about the fulcrum. This action causes the compression plate 308 to move toward the rigid housing which cradles the ventricles, forcing both ventricular free walls to approach the septum. Through its mechanism, stroke volume will increase proportional to compression plate 308 motion. Bellows 318 spring rates (about 2 lbs./in. for the inner and outer bellows 318) and ventricular filling pressures (about 10 mmHg) combine to retract the actuator 310 assist piston 316 during diastole and allow proper ventricular filling between assisted beats.

The assist device 302 will be completely assembled and connected to its hydraulic power source (e.g., muscle energy converter 10) prior to insertion into the chest cavity via a left thoracotomy. During implant the actuator 310 will be in the fully-retracted position so that the compression plate 308 is maximally separated from the pericardial shell 306, thereby forming the largest possible cavity for cardiac insertion. Placing the pericardial shell 306 beneath the apex of the heart 342, the device will be slid over both ventricles until the top of the shell 306 approximates the atrio-ventricular groove. The assist device 302 will be positioned so that the compression plate 308 lies over the left ventricular free wall opposite the septum. The assist device 302 will then be anchored to the sternum by passing heavy surgical wire through channels drilled in the rigid (titanium or titanium-related) shell 306 and looping them around the sternum (between the ribs) in a manner similar to the closure of a median sternotomy. Once the assist device 302 has been secured, pressure within the hydraulic line will be adjusted through an infusion port so that the compression plate 308 just contacts the left ventricle at end-diastole (so that diastolic filling will not be impaired). At this point, the assist device 302 will cradle both ventricles while leaving both left and right atria free. Following the successful completion of initial device testing, the surgeon will then close the thoracotomy in the standard fashion.

The motion of the levered compression plate 308 (LCP) is controlled by the assist device 302 actuator 310 assist piston 316 which, in turn, is governed by hydraulic forces transmitted via the MEC. During systole, the actuator 310 assist piston 316 extends from its housing and pushes the LCP 308 against the left ventricle (LV), thereby helping to eject blood from the heart 342. During diastole however, the LCP 308 can be returned to its set position through active or passive means—depending upon the nature of the actuator 310/compression plate 308 junction and the rate of assist piston 316 retraction. If this ball-and-socket junction is open, (i.e., able to separate) and the return forces of the MEC and assist device 302 bellows 318 are large enough, the actuator 310 assist piston head 340 (i.e., ball) will be pulled away from the LCP 308 socket during diastole, leaving the LCP 308 to retract passively against the expansion of the LV free wall as the heart 342 fills. Should the return forces of the MEC and assist device 302 fall below some critical level, contact will be maintained and cardiac preload pressures will contribute to actuator 310 retraction and MEC extension. If, on the other hand, the junction is closed (i.e., unable to separate) large bellows 318 forces would actively pull the plate 308 away from the heart 342, drawing the LV free wall away from the septum and enhancing cardiac filling. A closed junction combined with low bellows 318 return forces would, as in the open-junction case, cause cardiac preload pressures to contribute to actuator 310 retraction and MEC extension.

In order to provide the benefits of active filling derived from the closed-junction assist device 302, the muscle must supply enough power to both compress the ventricles and supply the bellows 318 with enough energy to both dilate the heart 342 and preload the muscle. If ample muscle power is available, a closed-junction system combined with large bellows 318 return forces could be used to aid the heart 342 both in systole and diastole. Otherwise, bellows 318 return forces must be minimized to conserve muscle power for systolic augmentation only—in which case closed and open-junction systems would function similarly.

The assembly of the assist device 302 hydraulic actuator 310 is as follows:

1. slide the metal bellows 318 into the actuator housing 336 (open end first);
2. place the first o-ring seal 332 beneath the upper rim of the metal bellows 318;
3. slide the assist support cylinder 334 into the actuator housing 336 so that it rests against the o-ring seal 332;
4. place the second o-ring seal 332 beneath the lower rim of the assist support cylinder 334;
5. screw the assist outlet port 326 onto the base of the actuator housing 336 so that the o-rings, bellows 318, and assist support cylinder 334 are pressed together to form a stable hydraulic seal.
6. center the diaphragm over the assist piston shaft 338 and screw the assist piston head 340 into the shaft so that the diaphragm is compressed between the two;
7. slide the assist piston 316/diaphragm 330 complex into the central aperture of the actuator housing 336;
8. rotate the assist piston 316 so that the shaft screws into the base of the metal bellows 318.

The assembly of assist device 302 structural components is as follows:

1. bring the base of the levered compression plate 308 (LCP) through the upper opening of the rigid pericardial shell 306 (RPS) so that the ball of the LCP 308 lies opposite the socket of the RPS;
2. snap the ball into the socket by applying pressure across the joint;
3. screw the hydraulic actuator 310 into the lower (threaded) RPS 306 aperture so that the outer flange of the diaphragm 330 is compressed between the RPS 306 and actuator housing 336;

To attach the hydraulic conduit 304 (tubing) to the actuator 310 assist outlet port 326:

1. slide the assist collet 324 over the conduit 304 with the threaded side positioned toward the assist device 302-end of the conduit 304;
2. slide the assist tined ferrule 328 over the conduit 304 with the tines facing away from the assist device 302-end of the conduit 304 (the assist tined ferrule 328 will be between the assist collet 324 and the end of the conduit 304);
3. push the conduit 304 over the barbs of the assist outlet port 326 until it contacts the main body of the port;
4. slide the base of the assist tined ferrule 328 into the recessed ring of the assist outlet port 326;
5. slide the assist collet 324 against the external threads of the assist outlet port 326 and secure by screwing the assist collet 324 onto the assist outlet port 326 until a tight fit is achieved(at this point, the conduit 304 will be held into place by the assist outlet port 326 barbs and the tines of the ferrule 328 which are being compressed against the conduit 304 wall by the assist collet 324).

Detailed operation of the MEC/assist device 302—a.k.a. muscle-actuated ventricular assist system 300 (MAVAS)

The following is a step-by-step description of MAVAS operation through one complete duty cycle, beginning with initial muscle activation following cardiac diastole.

1. At the beginning of cardiac systole (ventricular contraction), the implanted cardiomyostimulator senses the QRS complex of the heart 342 (via a right-ventricular sensing lead) and responds by sending a burst stimulus to the thoracodorsal (TD) nerve.
2. The TD nerve responds by activating the muscle fibers of the latissimus dorsi (LD) muscle, causing it to contract for the duration of the burst.
3. The LD pulls against the piston head 14 of the muscle energy converter 10 (MEC) causing the assist piston 204 to slide past the central bearing and pressurize the fluid surrounding the lower bellows 232 seal. As this occurs, the MEC outer bellows 230 is compressed and the inner bellows 232 extended. Through this mechanism, muscle force is converted to fluid pressure and muscle shortening to volume displacement.
4. Fluid pressure and displacement is transmitted directly to the assist device 302 actuator 310 through a low-compliance conduit 304 wherein the assist device 302 metal bellows 318 is compressed in response to the energy imparted by the fluid.
5. Compression of the assist device 302 bellows 318 causes the assist piston 316 to extend from the actuator housing 336 and impart a force at the interface between the assist piston head 340 and the levered compression plate 308 (LCP).
6. This force causes the LCP 308 to rotate about its interface with the pericardial shell 306 (a ball-and-socket joint) such that it pushes against the LV free-wall, forcing it to move toward the septum. The torque applied to the LCP

308 will be a direct function of muscle force generation. Likewise, the amount of rotation (LV compression) will depend on the degree of LD shortening (fluid volume displacement).

7. The motion of the LV free-wall causes blood to be pressurized and ejected from the LV cavity into the ascending aorta. The LV will remain compressed until the LD begins to relax (lengthen).

8. Following a pre-programmed period of activation, the burst stimulus to the muscle will be stopped and the muscle will begin to relax.

9. With the onset of LD relaxation, the force imparted by the muscle onto the MEC assist piston head 340 will rapidly decrease and the pressure within the conduit 304 will fall.

10. The compressed assist device 202 and MEC (outer) bellows 230 will then expand, forcing fluid from the assist device 202 back into the MEC, causing the assist device 202 assist piston 216 to move back into the actuator housing 236 and the MEC assist piston 204 to extend (returning the LD to its pre-contracted length)

11. During this expansion phase (step #10), the LCP 308 will be either actively drawn back toward its set position (in the closed-junction configuration) or allowed to move freely as the ventricles fill.

12. Passive expansion of the assist device 302 and extension of the MEC will continue until one of the following occurs:
   a. the inner MEC bellows 232 is completely compressed;
   b. the assist device 302 bellows 318 extends to contact the actuator 310 assist outlet port 326;
   c. the expansion forces (supplied by the compressed bellows 318 and 230) are balanced by the compression forces (supplied by the inner MEC bellows 232 and the stretched LD); or
   d. LD contraction is re-initiated via the cardiomyostimulator.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A system for assisting the operation of a patient's heart comprising:

a muscle energy converter which is capable of connecting to a muscle of the patient for converting energy of the muscle into a mechanical force; and a ventricular assist device connected to the muscle energy converter for receiving the mechanical force from the muscle energy converter and compressing the heart of the patient, the assist device comprises a shell having a continuous surface positioned about the heart which fits about the heart, a hinge, a compression plate which pivotably connects with the shell at the hinge, and an actuator, the assist device includes a conduit connected to the muscle energy converter, and fluid which is pumped by the muscle energy converter through the conduit to the actuator which receives the fluid and causes the actuator to press against the plate and pivot the plate against the heart in the shell to compress the heart, said assist device capable of connection and operational engagement with the heart.

2. The system as described in claim 1 wherein the shell has an open face through which the plate pushes against the heart.

3. A system as described in claim 2 wherein the plate forms a ball and socket connection with the shell at the hinge.

4. The system is described in claim 3 wherein the actuator comprises an assist piston which presses against the plate forcing the plate against the heart, said piston in contact with the plate.

5. The system is described in claim 4 wherein the actuator includes bellows in which the assist piston is housed, said bellows is compressed by the fluid pumped by the muscle energy converter which in turn pushes the assist piston against the plate, said bellows positioned about the piston.

6. A method for assisting the operation of the patient's heart comprising the steps of:

converting energy from a muscle to a mechanical force with a muscle energy converter; and compressing the heart of the patient with an assist device with the mechanical force from the muscle energy converter, by fluid moved by the muscle energy converter through a conduit connected between the muscle energy converter and the assist device pushing a plate against the heart in a shell positioned about the heart to pump blood in the heart.

* * * * *